(12) United States Patent
Falak et al.

(10) Patent No.: US 7,977,539 B2
(45) Date of Patent: Jul. 12, 2011

(54) *SCLEROTINIA*-RESISTANT *BRASSICA*

(75) Inventors: Igor Falak, Guelph (CA); Lomas Tulsieram, Mississauga (CA); Jayantilal Patel, Thornhill (CA); Dave Charne, Guelph (CA)

(73) Assignee: Pioneer Hi Bred International Inc, Johnston, IA (US)

( * ) Notice: Subject to any disclaimer, the term of this patent is extended or adjusted under 35 U.S.C. 154(b) by 247 days.

(21) Appl. No.: 12/174,134

(22) Filed: Jul. 16, 2008

(65) Prior Publication Data

US 2008/0280013 A1    Nov. 13, 2008

Related U.S. Application Data

(62) Division of application No. 11/422,623, filed on Jun. 7, 2006.

(60) Provisional application No. 60/688,687, filed on Jun. 9, 2005.

(51) Int. Cl.
*A01H 1/00* (2006.01)
*A01H 1/02* (2006.01)
*A01H 5/00* (2006.01)
*A01H 5/10* (2006.01)
*C12N 5/04* (2006.01)

(52) U.S. Cl. ........ 800/306; 800/260; 800/301; 800/303; 800/298; 800/295; 435/419; 435/468; 435/410

(58) Field of Classification Search .......................... None
See application file for complete search history.

(56) References Cited

FOREIGN PATENT DOCUMENTS

WO    02061043 A2    8/2002
WO    2005000007 A2    1/2005

OTHER PUBLICATIONS

Kim et al. Crop Science (2000) 40:55-61.*
Arahana et al. Crop Science, (2001) 41:180-188.*
Liu, S., et al.; "In vitro mutation and selection of double-haploid *Brassica napus* lines with improved resistance to *Sclerotinia sclerotiorum*" Plant Cell Rep (2005) 24:133-1344; Springer-Verlag, Berlin/Heidelberg, Germany.
Mullins, E., et al.; "Isolation of mutants exhibiting altered resistance to *Sclerotinia sclerotiorum* from small M2 populations of an oilseed rape (*Brassica napus*) variety"; European Journal of Plant Pathology (1999) 105:465-475; Springer; The Netherlands.
Bradley, C.A., et al.; "Response of canola cultivars to *Sclerotinia sclerotiorum* in controlled and field environments"; Plant Disease (2006) 90:215-219; APS Press, USA.
Zhao, J., et al.; "Elvaulation of *Sclerotinia* stem rot resistance in oilseed *Brassica napus* using a petiole inoculation technique under greenhouse conditions"; Plant Disease (2004) 88:1033-1039; APS Press, US.
Auclair, J., et al.; "Development of a new field inoculation technique to assess partial resistance in soybean to *Sclerotinia sclerotiorum*"; Canadian Journal of Plant Science (Jan. 2004) 84(1):57-64; Agricultural Institute of Canada; Ottawa, CA.
Bardin, S.D., et al.; "Research on biology and control of *Sclerotinia* diseases in Canada"; Can J Plant Pathol (2001) 23:88-98; Canadian Phytopathological Society, Canada.
Fitt, B.D.L., et al.; "World-wide importance of phoma stem canker (*Leptosphaeria maculans* and *L. biglobosa*) on oilseed rape (*Brassica napus*)"; European Journal of Plant Pathology (2006) 114:3-15; Springer, The Netherlands.
Zhao, J., et al.; "Detection of loci controlling seed glucosinolate content and their association with *Sclerotinia* resistance in *Brassica napus*"; Plant Breeding (2003) 122:19-23; Blackwell Verlag; Berlin, Germany.

* cited by examiner

*Primary Examiner* — Medina A Ibrahim

(57) ABSTRACT

The invention provides *Brassica* plants and lines having an improved *Sclerotinia sclerotiorum* Disease Incidence (SSDI %) score and represented by, or descended from, NCIMB Accession Number 41388 or 41390.

12 Claims, 8 Drawing Sheets

| Variety | Days to 50% flower | Maturity | Lodging | SSDI score | % 46A76 | %46A65 | % of check mean |
|---|---|---|---|---|---|---|---|
| 02SN41269[4] | 45.6 | 92.6 | 3.94 | 32 | 55 | 55 | 55 |
| 04DHS12921[2] | 45.3 | 93.1 | 4.00 | 26 | 47 | 43 | 45 |
| 04DHS11319[2] | 46.3 | 94.8 | 4.38 | 24 | 44 | 40 | 42 |
| 04SN41415[2] | 45.1 | 92.4 | 5.06 | 23 | 42 | 38 | 40 |
| 46A65[4] | 45.6 | 94.9 | 5.13 | 58 | 99 | 100 | 99 |
| 03SN40341[4] | 45.8 | 97.2 | 5.13 | 27 | 47 | 46 | 47 |
| 03SN40441[4] | 45.3 | 96.5 | 5.63 | 25 | 43 | 43 | 43 |
| 04DHS11418[2] | 47.3 | 97.5 | 5.94 | 27 | 49 | 45 | 47 |
| 04SN41433[2] | 46.3 | 97.2 | 6.06 | 15 | 27 | 25 | 26 |
| 46A76[4] | 47.5 | 98.4 | 6.31 | 59 | 100 | 102 | 101 |
| 05DHS12879[1] | n/a | n/a | n/a | 7 | 12 | 10 | 11 |
| 05DHS12897[1] | n/a | n/a | n/a | 12 | 20 | 17 | 19 |

Figure 2A. Extreme disease pressure field research data.
[1, 2, 4]*Sclerotinia* data generated at 1, 2, or 4 locations, respectively. Lodging scored (1 lodged, 9 erect) at 4 locations.
Flowering and maturity data generated at 3 locations.

| Variety | SSDI | %46A76 | %46A65 | % of check mean |
|---|---|---|---|---|
| 02SN41269[3] | 11 | 68 | 29 | 49 |
| 04DHS12921[1] | 24 | 147 | 49 | 98 |
| 04DHS11319[1] | 36 | 222 | 74 | 148 |
| 04SN41415[1] | 12 | 72 | 24 | 48 |
| 46A65[3] | 38 | 232 | 100 | 166 |
| 03SN40341[3] | 9 | 55 | 24 | 40 |
| 03SN40441[3] | 8 | 50 | 22 | 36 |
| 04DHS11418[1] | 12 | 72 | 24 | 48 |
| 04SN41433[1] | 8 | 50 | 17 | 33 |
| 46A76[3] | 16 | 100 | 43 | 72 |
| 05DHS12879 | n/a | n/a | n/a | n/a |
| 05DHS12897 | n/a | n/a | n/a | n/a |
| | | | | |

Figure 2B. Natural field data.

[1, 3]Data generated at 1 or 3 locations, respectively.

| VARIETY | SSDI | %46A76 | % 46A65 | % of check mean |
|---|---|---|---|---|
| 02SN41269[7] | 23 | 61 | 44 | 52 |
| 04DHS12921[3] | 25 | 80 | 45 | 63 |
| 04DHS11319[3] | 28 | 103 | 51 | 77 |
| 04SN41415[3] | 19 | 52 | 34 | 43 |
| 46A65[7] | 49 | 156 | 100 | 128 |
| 03SN40341[7] | 19 | 51 | 37 | 44 |
| 03SN40441[7] | 18 | 46 | 34 | 40 |
| 04DHS11418[3] | 22 | 57 | 38 | 47 |
| 04SN41433[3] | 13 | 35 | 22 | 29 |
| 46A76[7] | 41 | 100 | 77 | 88 |
| 05DHS12879[1] | 7 | 12 | 10 | 11 |
| 05DHS12897[1] | 12 | 20 | 17 | 19 |
| | | | | |

Figure 2C. Combined extreme research and natural field data.
[1, 3, 7]Data generated at 1, 3, or 7 locations, respectively.

| Variety | SSDI | %46A76 | %46A65 | % of check mean |
|---|---|---|---|---|
| 02SN41269 | 3 | 16 | 8 | 12 |
| 04DHS12921 | | | | |
| 04DHS11319 | | | | |
| 04SN41415 | | | | |
| 46A65 | 33 | 198 | 100 | 149 |
| 03SN40341 | 4 | 23 | 12 | 17 |
| 03SN40441 | 2 | 14 | 7 | 10 |
| 04DHS11418 | | | | |
| 04SN41433 | | | | |
| 46A76 | 16 | 100 | 50 | 75 |
| 05DHS12879 | n/a | n/a | n/a | n/a |
| 05DHS12897 | n/a | n/a | n/a | n/a |

Figure 2D. Natural field data; NDSU 2005 data omitted.
Data generated at 2 locations only.

| VARIETY | SSDI | % 46A76 | %46A65 | % of check mean |
|---|---|---|---|---|
| 02SN41269[6] | 22 | 42 | 39 | 41 |
| 04DHS12921[2] | 26 | 47 | 43 | 45 |
| 04DHS11319[2] | 24 | 44 | 40 | 42 |
| 04SN41415[2] | 23 | 42 | 38 | 40 |
| 46A65[6] | 50 | 132 | 100 | 116 |
| 03SN40341[6] | 19 | 39 | 35 | 37 |
| 03SN40441[6] | 17 | 34 | 31 | 32 |
| 04DHS11418[2] | 27 | 49 | 45 | 47 |
| 04SN41433[2] | 15 | 27 | 25 | 26 |
| 46A76[6] | 45 | 100 | 85 | 92 |
| 05DHS12879[1] | 7 | 12 | 10 | 11 |
| 05DHS12897[1] | 12 | 20 | 17 | 19 |

Figure 2E. Combined extreme research and natural field data; NDSU 2005 data omitted.

[1, 2, 6] Data generated at 1, 2, or 6 locations, respectively.

SCLEROTINIA-RESISTANT BRASSICA

REFERENCE TO RELATED APPLICATIONS

This application is a divisional of U.S. application Ser. No. 11/422,623 filed Jun. 7, 2006, which claims priority to U.S. provisional application 60/688,687 filed Jun. 9, 2005, both of which are hereby incorporated by reference.

TECHNICAL FIELD

The present invention relates to *Sclerotinia* resistant *Brassica*.

BACKGROUND OF THE INVENTION

*Sclerotinia* infects over 100 species of plants, including numerous economically important crops such as *Brassica* species, sunflowers, dry beans, soybeans, field peas, lentils, lettuce, and potatoes (Boland and Hall, 1994). *Sclerotinia sclerotiorum* is responsible for over 99% of *Sclerotinia* disease, while *Sclerotinia minor* produces less than 1% of the disease. *Sclerotinia* produces sclerotia, irregularly-shaped, dark overwintering bodies, which can endure in soil for four to five years. The sclerotia can germinate carpogenically or myceliogenically, depending on the environmental conditions and crop canopies. The two types of germination cause two distinct types of diseases. Sclerotia that germinate carpogenically produce apothecia and ascospores that infect above-ground tissues, resulting in stem blight, stalk rot, head rot, pod rot, white mold, and blossom blight of plants. Sclerotia that germinate myceliogenically produce mycelia that infect root tissues, causing crown rot, root rot and basal stalk rot.

*Sclerotinia* causes *Sclerotinia* stem rot, also known as white mold, in *Brassica*, including canola. Canola is a type of *Brassica* having a low level of glucosinolates and erucic acid in the seed. The sclerotia germinate carpogenically in the summer, producing apothecia. The apothecia release wind-borne ascospores that travel up to one kilometer. The disease is favoured by moist soil conditions (at least 10 days at or near field capacity) and temperatures of 15-25° C., prior to and during canola flowering. The spores cannot infect leaves and stems directly; they must first land on flowers, fallen petals, and pollen on the stems and leaves. Petal age affects the efficiency of infection, with older petals more likely to result in infection (Heran, et al., 1999). The fungal spores use the flower parts as a food source as they germinate and infect the plant.

The severity of *Sclerotinia* in *Brassica* is variable, and is dependent on the time of infection and climatic conditions (Heran, et al., 1999). The disease is favored by cool temperatures and prolonged periods of precipitation. Temperatures between 20 and 25° C. and relative humidities of greater than 80% are required for optimal plant infection (Heran, et al., 1999). Losses ranging from 5 to 100% have been reported for individual fields (Manitoba Agriculture, Food and Rural Initiatives, 2004). On average, yield losses equal 0.4 to 0.5 times the percentage infection. For example, if a field has 20% infection (20/100 infected plants), then the yield loss would be about 10%. Further, *Sclerotinia* can cause heavy losses in wet swaths. *Sclerotinia sclerotiorum* caused economic losses to canola growers in Minnesota and North Dakota of 17.3, 20.8 and 16.8 million dollars in 1999, 2000, and 2001, respectively. (Bradley, et al. 2006)

The symptoms of *Sclerotinia* infection usually develop several weeks after flowering begins. The plants develop pale-grey to white lesions, at or above the soil line and on upper branches and pods. The infections often develop where the leaf and the stem join because the infected petals lodge there. Once plants are infected, the mold continues to grow into the stem and invade healthy tissue. Infected stems appear bleached and tend to shred. Hard black fungal sclerotia develop within the infected stems, branches, or pods. Plants infected at flowering produce little or no seed. Plants with girdled stems wilt and ripen prematurely. Severely infected crops frequently lodge, shatter at swathing, and make swathing more time consuming. Infections can occur in all above-ground plant parts, especially in dense or lodged stands, where plant-to-plant contact facilitates the spread of infection. New sclerotia carry the disease over to the next season.

Conventional methods for control of *Sclerotinia* diseases include (a) chemical control, (b) disease resistance and (c) cultural control, each of which is described below.

(a) Fungicides such as benomyl, vinclozolin and iprodione remain the main method of control of *Sclerotinia* disease (Morall, et al., 1985; Tu, 1983). Recently, additional fungicidal formulations have been developed for use against *Sclerotinia*, including azoxystrobin, prothioconazole, and boscalid. (Johnson, 2005) However, use of fungicide is expensive and can be harmful to the user and environment. Further, resistance to some fungicides has occurred due to repeated use.

(b) In certain cultivars of bean, safflower, sunflower and soybean, some progress has been made in developing partial (incomplete) resistance. Partial resistance is often referred to as tolerance. However, success in developing partial resistance has been very limited, probably because partial physiological resistance is a multigene trait as demonstrated in bean (Fuller, et al., 1984). In addition to partial physiological resistance, some progress has been made to breed for morphological traits to avoid *Sclerotinia* infection, such as upright growth habit, lodging resistance and narrow canopy. For example, bean plants with partial physiological resistance and with an upright stature, narrow canopy and indeterminate growth habit were best able to avoid *Sclerotinia* (Saindon, et al., 1993). Early maturing cultivars of safflower showed good field resistance to *Sclerotinia*. Finally, in soybean, cultivar characteristics such as height, early maturity and great lodging resistance result in less disease, primarily because of a reduction of favorable microclimate conditions for the disease. (Boland and Hall, 1987; Buzzell, et al., 1993)

(c) Cultural practices such as using pathogen-free or fungicide-treated seed, increasing row spacing, decreasing seeding rate to reduce secondary spread of the disease, and burying sclerotia to prevent carpogenic germination may reduce *Sclerotinia* disease but not effectively control the disease.

All Canadian canola genotypes are susceptible to *Sclerotinia* stem rot (Manitoba Agriculture, Food and Rural Initiatives, 2004). This includes all known spring petalled genotypes of canola quality. There is also no resistance to *Sclerotinia* in Australian canola varieties. (Hind-Lanoiselet, et al., 2004) Some varieties with certain morphological traits are better able to withstand *Sclerotinia* infection. For example, Polish varieties (*Brassica rapa*) have lighter canopies and seem to have much lower infection levels. In addition, petal-less varieties (apetalous varieties) avoid *Sclerotinia* infection to a greater extent (Okuyama, et al., 1995; Fu, 1990). Other examples of morphological traits which confer a degree of reduced field susceptibility in *Brassica* genotypes include increased standability, reduced petal retention, branching (less compact and/or higher), and early leaf abscission. Jurke and Fernando, (2003) screened eleven canola genotypes for *Sclerotinia* disease incidence. Significant variation in disease incidence was explained by plant morphology, and the difference in petal retention was identified as the most important factor. However, these morphological traits alone do not confer resistance to *Sclerotinia*, and all canola products in Canada are considered susceptible to *Sclerotinia*.

Winter canola genotypes are also susceptible to *Sclerotinia*. In Germany, for example, no *Sclerotinia*-resistant varieties are available. (Specht, 2005) The widely-grown German variety Express is considered susceptible to moderately susceptible and belongs to the group of less susceptible varieties/hybrids. (See, Table 4)

Spraying with fungicide is the only means of controlling *Sclerotinia* in canola crops grown under disease-favorable conditions at flowering. Typical fungicides used for controlling *Sclerotinia* on *Brassica* include Rovral™ from Bayer and Ronilan™/Lance™ from BASF. The active ingredient in Lance™ is Boscalid, and it is marketed as Endura™ in the United States. The fungicide should be applied before symptoms of stem rot are visible and usually at the 20-30% bloom stage of the crop. If infection is already evident, there is no use in applying fungicide as it is too late to have an effect. Accordingly, growers must assess their fields for disease risk to decide whether to apply a fungicide. This can be done by using a government provided checklist or by using a petal testing kit. Either method is cumbersome and prone to errors. (Hind-Lanoiselet, 2004; Johnson, 2005)

Numerous efforts have been made to develop *Sclerotinia* resistant *Brassica* plants. Built-in resistance would be more convenient, economical, and environmentally-friendly than controlling *Sclerotinia* by application of fungicides. Since the trait is polygenic it would be stable and not prone to loss of efficacy, as fungicides may be.

Spring canola (*Brassica napus* subsp. *oleifera* var. *annua*) differs from winter canola (*Brassica napus* subsp. *oleifera* var. *biennis*) primarily in the absence of an obligate vernalization requirement. Asiatic rapeseed, and canola versions, have a low to intermediate requirement for vernalization, and are known as semi-winter types. While winter canola cannot finish its reproduction cycle when planted in the spring, early spring planting and exposure to cold enables Asiatic material to flower and set seed. Asiatic material cannot finish its reproduction cycle if planted in late spring. In controlled conditions, winter material requires 12-14 weeks of vernalization while Asiatic material requires 2-8 weeks. Table 1 summarizes the differences between winter, semi-winter (Asiatic) and spring canola varieties.

TABLE 1

Main determinations of growth habit in *Brassica napus* materials

| Type | Spring* | Spring | Semi Winter (Asiatic) | Winter |
| --- | --- | --- | --- | --- |
| Growing areas | Canada, Europe | Australia | China, Japan | Europe |
| Vernalization Requirement | None | None | 2-8 weeks intermediate | 12-14 weeks strong or full |
| Time of seeding | Spring (Increasing Day Length) | Fall (Decreasing Day Length) | Fall (Decreasing Day Length) | Fall (Decreasing Day Length) |
| Number of days until flowering | 30-90 | 90-150 | 120-180 | 150-270 |

*Canadian, European and Australian spring materials can be planted and grown in any environment or seeding time for spring canola.

Some Chinese (semi-winter) cultivars of rapeseed/canola are partially resistant to *Sclerotinia*. For example, ChunYun, et al., 2003; HanZhong, et al., 2004; XeiXin, et al., 2002; YongJu et al., 2000; ChaoCai, et al., 1998 describe partially resistant varieties of rapeseed. However, some of these varieties are not canola quality, and all of them require vernalization. The partial field resistance in Chinese varieties originated mostly from the rapeseed variety Zhong you 821. Despite improvements in partial resistance in Zhong you 821, its reaction to disease is less stable under environmental conditions favorable for development of *Sclerotinia* (Yunchang, et al., 1999). This indicates a lower level of partial resistance (Li, et al., 1999).

Some Japanese cultivars of rapeseed have partial stem resistance to *Sclerotinia*. Partial stem resistance was detected by indoor tests in comparison with winter canola (Brun, et al., 1987). However, these varieties are not canola quality and are semi-winter types (see, Table 1).

Breeding for *Sclerotinia* field resistance in canola has been very difficult due to the quantitative nature of this trait. Further, the incorporation of physiological resistance with morphological traits that avoid or reduce infection multiplies the complexity of breeding for resistance. In addition, it has been very difficult to screen for resistance because of the direct environment interaction (i.e., temperature and humidity requirements, as well as microenvironment requirements) with the plant population. As stated above, there are no Canadian spring *Brassica* varieties with resistance to *Sclerotinia*, this despite many years of co-evolution and environmental pressure to select for this trait. The highest available level of field resistance in rapeseed (and recently some canola materials) was attained via breeding efforts in China as described with Zhong you 821 (Yunchang, et al., 1999). The levels of such partial resistance or tolerance are relatively low as fungicide applications are still recommended on all rapeseed and canola materials in China (verbal communication) (Baocheng, et al., 1999). Clearly, *Brassica* and canola varieties with high levels of resistance to *Sclerotinia* are not found in nature.

Canola quality *Brassica napus* was developed in the 1970's. Despite 30 years of extensive breeding efforts, no canola varieties resistant to *Sclerotinia* have previously been developed. The breeding efforts included quantitative trait loci analysis (Zhao-Jianwei, et al., 2003), mutagenesis breeding (Mullins, et al., 1999; Wu-Yanyou, et al., 1996; Liang-Hong, et al., 2003), extensive screening efforts (Sedune, et al., 1989; Zhao, et al., 2004); and screening for expressed sequence tags (ESTs) (Rugang, et al., 2004), to name a few. Several spring canola varieties with moderate tolerance to *Sclerotinia* have been developed (Ahmadi, et al., 2000a; Ahmadi, et al., 2000b; BaoMing, et al., 1999; and Liu, et al., 1991), however the level of tolerance is low and the lines cannot withstand high disease pressure. Recently, transgenic canola has been developed carrying an oxalic oxidase gene (U.S. Pat. No. 6,166,291 and divisional patents thereof); however there are regulatory and social issues associated with transgenic plants. Winter canola genotypes with resistance to *Sclerotinia* are also needed as indicated by fungicide applications (Johnson, 2005). Accordingly, significant technical human intervention is required to breed canola varieties that are resistant to *Sclerotinia*.

SUMMARY OF THE INVENTION

An aspect of the present invention is to provide a *Brassica* plant or group of plants with improved resistance to *Sclerotinia sclerotiorum*. In one aspect, the invention provides a spring *Brassica napus* plant or group of plants, the plant or group of plants being representative of a population wherein the population has an average *Sclerotinia sclerotiorum* Disease Incidence (SSDI %) score which is less than about 60% of the SSDI % score of Pioneer Hi-Bred variety 46A76, or of Pioneer Hi-Bred variety 46A65, or of the mean SSDI % score of the two varieties, under the same environmental and disease conditions in the field. The *Brassica napus* plant or group of plants may also be representative of a population wherein the population has an average *Sclerotinia sclerotiorum* Disease Incidence (SSDI %) score which is less than 50%, 35% or 20% of the score of Pioneer Hi-Bred variety 46A76 or of Pioneer Hi-Bred variety 46A65 or of the mean score of the two varieties.

Another aspect of the present invention is to provide a winter *Brassica napus* plant or group of plants, the plant or group of plants being representative of a population wherein the population has an average *Sclerotinia sclerotiorum* Disease Incidence (SSDI %) score which is less than about 60% of the SSDI % score of the variety Columbus, or of the variety Express, or of the mean SSDI % score of the two varieties, under the same environmental and disease conditions in the field. The winter *Brassica napus* plant or group of plants may also be representative of a population wherein the population has an average *Sclerotinia sclerotiorum* Disease Incidence (SSDI %) score which is less than 50%, 35% or 20% of the score of the variety Columbus or of the variety Express or of the mean score of the two varieties.

Another aspect of the present invention is to provide a spring *Brassica napus* plant or group of plants, the plant or group of plants representing a population characterized by at least the following traits: (a) a solid component of the seed of the population comprising a glucosinolate level of less than 30 μmoles per gram of oil-free solid, (b) oil of the seed of the plant comprising less than 2% erucic acid, (c) a 50% flowering time of between about 30 to 90 days, and (d) an SSDI % score which is less than about 60% of the SSDI % score of Pioneer Hi-Bred variety 46A76, or of Pioneer Hi-Bred variety 46A65, or of the mean score of the two varieties, under the same environmental and disease conditions in the field. The *Brassica napus* plant may also be representative of a population wherein the population has an average *Sclerotinia sclerotiorum* Disease Incidence (SSDI %) score which is less than 50%, 35% or 20% of the score of Pioneer Hi-Bred variety 46A76 or of Pioneer Hi-Bred variety 46A65 or of the mean score of the two varieties.

Another aspect of the present invention is to provide a winter *Brassica napus* plant or group of plants, the plant or group of plants representing a population characterized by at least the following traits: (a) a solid component of the seed of the population comprising a glucosinolate level of less than 30 μmoles per gram of oil-free solid, (b) oil of the seed of the population comprising less than 2% erucic acid, (c) a 50% flowering time of between about 30 to 90 days, and (d) an SSDI % score which is less than about 60% of the SSDI % score of the variety Columbus, or of the variety Express, or of the mean SSDI % score of the two varieties, under the same environmental and disease conditions in the field. The winter *Brassica napus* plant or group of plants may also be representative of a population wherein the population has an average *Sclerotinia sclerotiorum* Disease Incidence (SSDI %) score which is less than 50%, 35% or 20% of the score of the variety Columbus or of the variety Express or of the mean score of the two varieties.

The *Brassica napus* plant may represent a spring *Brassica napus* line as follows:
(a) an S3 bulk increase of 03SN40341, deposited under ATCC accession no. PTA-6776; or a doubled-haploid line derived from 03SN40341 and deposited under ATCC accession no. PTA-6780.
(b) an S3 bulk increase of 03SN40441, deposited under ATCC accession no. PTA-6779; or a doubled-haploid line derived from 03SN40441 and deposited under ATCC accession no. PTA-6778.
(c) an F4 bulk increase of 02SN41269, deposited under ATCC accession no. PTA-6777; or a doubled-haploid line derived from 02SN41269 and deposited under ATCC accession no. PTA-6781.
(d) An S2 bulk designated 04SN41433, deposited under NCIMB accession no. 41389 or a doubled-haploid line derived from 04SN41433 and deposited under NCIMB accession no. 41391.
(e) an S2 bulk designated 04SN41415, deposited under NCIMB accession no. 41388, or a doubled-haploid line derived from 04SN41415 and deposited under NCIMB accession no. 41390.
(See also, Table 11a.)

The *Brassica napus* plant may represent a winter *Brassica napus* line as follows:
(a) an F4 bulk increase of line 04CWB930128, deposited under NCIMB accession no. 41396.
(b) an F4 bulk increase of line 04CWB930127, deposited under NCIMB accession no. 41395.
(c) an F4 bulk increase of line 04CWB930081, deposited under NCIMB accession no. 41393.
(d) an F4 bulk increase of line 04CWB930111, deposited under NCIMB accession no. 41394.
(e) an F4 bulk increase of line 04CWB930144, deposited under NCIMB accession no. 41398
(f) an F4 bulk increase of line 04CWB930015, deposited under NCIMB accession no. 41392.
(g) an F4 bulk increase of line 04CWB930135, deposited under NCIMB accession no. 41397.
(See also, Table 11b.)

Another aspect of the present invention is to provide a descendent plant of any of the *Brassica* plants of the above-mentioned aspects, wherein the descendent plant is characterized by at least the following traits: (a) a solid component of the seed of the plant comprising a glucosinolate level of less than 30 μmoles per gram of oil-free solid, (b) oil of the seed of the plant comprising less than 2% erucic acid, (c) a 50% flowering time of between about 30 to 90 days, and (d) being representative of a population having an SSDI % score which is less than about 60% of the SSDI % score (1) of Pioneer Hi-Bred variety 46A76, or of Pioneer Hi-Bred variety 46A65, or of the mean score of the two varieties, where the descendent plant has a spring growth habit, or (2) of the SSDI % score of the variety Columbus, or of the variety Express, or of the mean SSDI % score of the two varieties, where the descendent plant has a winter growth habit, under the same environmental and disease conditions in the field. The descendent *Brassica napus* plant may also represent a population having an average level of *Sclerotinia* incidence of less than 50%, 35% or 20% of the SSDI % score of (1) Pioneer Hi-Bred variety 46A76 or Pioneer Hi-Bred variety 46A65 or the mean score of the two varieties, where the descendent plant has a spring growth habit, or (2) the variety Columbus or the variety Express or the mean score of the two varieties, where the descendent plant has a winter growth habit, under the same environmental and disease conditions in the field.

Another aspect of the invention is to provide a *Brassica napus* plant or group of plants, the plant or group of plants having physiological traits, or a combination of morphological and physiological traits functioning in synchrony, to reduce disease development, wherein the plant or group of plants is representative of a population, said population having an SSDI % score which is less than about 60% of the SSDI % score of (1) Pioneer Hi-Bred variety 46A76, or Pioneer Hi-Bred variety 46A65, or the mean score of the two varieties, where the population has a spring growth habit, or (2) the variety Columbus or the variety Express or the mean score of the two varieties, where the population has a winter growth habit, under the same environmental and disease conditions in the field.

Another aspect of the invention is to provide progeny of any of the *Brassica napus* plants discussed above, said progeny produced by extracting the *Sclerotinia* resistant trait by doubled haploidy, and wherein a homogeneous population comprising said progeny has an SSDI % score which is less than about 60% of the SSDI % score of (1) Pioneer Hi-Bred variety 46A76 or Pioneer Hi-Bred variety 46A65 or the mean score of the two varieties, where the population has a spring growth habit, or (2) the variety Columbus or the variety Express or the mean score of the two varieties, where the population has a winter growth habit, under the same environmental and disease conditions in the field.

Further, the invention also provides a doubled haploid line produced from any of the *Brassica napus* plants discussed above, seed from any of the plants, crushed *Brassica napus* seed from any of the plants, plant cells from any of the plants, and cellular plant material from any of the plants, for example, pollen or ovule material.

Another aspect of the invention is to provide a method for screening for resistance of a plant to *Sclerotinia* under controlled environmental conditions, comprising, (a) inoculating the plant growing in controlled environmental conditions with a low-nutrient PDA plug comprising mycelium of *Sclerotinia*, and (b) screening for resistance of the plant to *Sclerotinia*. The plug may be attached to the plant by an entomological needle. The plug may be about 3 mm. The controlled environmental conditions may comprise controlled humidity.

Another aspect of the invention is to provide a method for screening a plant growing in the field for resistance to *Sclerotinia*, comprising, (a) inoculating the plant with *Sclerotinia*, (b) irrigating the plant with water, wherein the water is low in, or free of, ions which could bind with oxalic acid; (c) maintaining a pre-determined threshold of continuous wetness on the plant, and (d) screening for resistance of the plant to *Sclerotinia*. Inoculation may be accomplished using a carrier material. The carrier may be seed, such as Niger seed, colonized with *Sclerotinia*, and may be disseminated at a rate of about 5-20 kg/ha. The water may be deionized water, distilled water, runoff water or collected rainwater. The method may further comprise use of a netting enclosure to provide a controlled microenvironment.

Another aspect of the invention is to provide a method of producing a successive generation of a *Brassica napus* line 03SN40341 having an SSDI % score which is less than about 60% of the SSDI % score of Pioneer Hi-Bred variety 46A76, or of Pioneer Hi-Bred variety 46A65, or of the mean score of the two varieties, under the same environmental and disease conditions in the field, comprising, (a) crossing *Brassica napus* line 03SN40341 with itself or with another *Brassica* plant to yield a *Brassica* line 03SN40341-derived progeny *Brassica* seed, (b) growing the *Brassica napus* seed of step (a) to yield an additional *Brassica* line 03SN40341-derived *Brassica* plant, (c) optionally repeating the crossing and growing of steps (a) and (b) for successive generations to produce further plants derived from *Brassica napus* line 03SN40341, and (d) selecting a descendent plant wherein a said plant represents a population of plants having an SSDI % score which is less than about 60% of the SSDI % score of Pioneer Hi-Bred variety 46A76, or of Pioneer Hi-Bred variety 46A65, or of the mean score of the two varieties, under the same environmental and disease conditions in the field. The invention also provides similar methods for lines 03SN40441, 02SN41269, 04DHS12921, 04DHS11319, 04DHS11418, 04SN41433, 04SN41415, 05DHS12897, and 04DHS12879. A population represented by the descendent plant may have an SSDI % score which is less than about 50%, 35%, or 20% of the SSDI % score of Pioneer Hi-Bred variety 46A76, or of Pioneer Hi-Bred variety 46A65, or of the mean score of the two varieties, under the same environmental and disease conditions in the field.

Another aspect of the invention is to provide a method of producing a successive generation of a *Brassica napus* line 04CWB930127 having an SSDI % score which is less than about 60% of the SSDI % score of the variety Columbus, or of the variety Express, or of the mean score of the two varieties, under the same environmental and disease conditions in the field, comprising, (a) crossing *Brassica napus* line 04CWB930127 with itself or with another *Brassica* plant to yield a *Brassica* line 04CWB930127-derived progeny *Brassica* seed, (b) growing the *Brassica napus* seed of step (a) to yield an additional *Brassica* line 04CWB930127-derived *Brassica* plant, (c) optionally repeating the crossing and growing of steps (a) and (b) for successive generations to produce further plants derived from *Brassica napus* line 04CWB930127, and (d) selecting a descendent plant wherein said plant represents a population of plants having an SSDI % score which is less than about 60% of the SSDI % score of the variety Columbus or the variety Express or the mean score of the two varieties, under the same environmental and disease conditions in the field. The invention also provides similar methods for lines 04CWB930128, 04CWB930081, 04CWB930111, 04CWB930144, 04CWB930135, and 04CWB930015. A population represented by the descendent plant may have an SSDI % score which is less than about 50%, 35%, or 20% of the SSDI % score of the variety Columbus or the variety Express or the mean of the two varieties, under the same environmental and disease conditions in the field.

Another aspect of the present invention is to provide use of a spring *Brassica napus* plant, the plant being representative of a population which has an SSDI % score which is less than about 60% of the SSDI % score of Pioneer Hi-Bred variety 46A76, or of Pioneer Hi-Bred variety 46A65, or of the mean score of the two varieties, under the same environmental and disease conditions in the field, for growing a crop, for oil and meal production, or for breeding a new *Brassica* line. The plant may be designated 03SN40341, 03SN40441, 02SN41269, 04DHS12921, 04DHS11319, or 04DHS11418, representative seed being deposited under ATCC accession no: PTA-6776, PTA-6779, PTA-6777, PTA-6781, PTA-6780, or PTA-6778, respectively, said seed deposited on or about Jun. 8, 2005; or may be designated 04SN41433, 04SN41415, 05DHS12897, or 04DHS12879, representative seed being deposited under NCIMB accession no 41389, 41388, 41391, or 41390, respectively.

Another aspect of the present invention is to provide use of a winter *Brassica napus* plant, the plant being representative of a population which has an SSDI % score which is less than about 60% of the SSDI % score of the variety Columbus, or of the variety Express, or of the mean score of the two varieties, under the same environmental and disease conditions in the field, for growing a crop, for oil and meal production, or for breeding a new *Brassica* line. The plant may be designated 04CWB930127, 04CWB930128, 04CWB930081, 04CWB930111, 04CWB930144, 04CWB930135, or 04CWB930015, representative seed being deposited under NCIMB accession no: 41395, 41396, 41393, 41394, 41398, 41397, or 41392, respectively.

Another aspect of the present invention is to provide a method of producing a canola oil, comprising (a) crushing seeds produced by a *Brassica napus* plant which may be designated 03SN40341, 03SN40441, 02SN41269, 04DHS12921, 04DHS11319, or 04DHS11418, representative seed being deposited under ATCC accession no: PTA-6776, PTA-6779, PTA-6777, PTA-6781, PTA-6780, or PTA-6778, respectively, said seed deposited on or about Jun. 8, 2005; or may be designated 04SN41433, 04SN41415, 05DHS12897, or 04DHS12879, representative seed being deposited under NCIMB accession no. 41389, 41388, 41391, or 41390, respectively; or a descendent of any said plants, wherein the plant or descendent plant is representative of a population having an SSDI % score which is less than about 60% of the SSDI % score of Pioneer Hi-Bred variety 46A76, or of Pioneer Hi-Bred variety 46A65, or of the mean score of the two varieties, under the same environmental and disease conditions in the field, (b) extracting a crude oil from said crushed seeds, and optionally (c) refining, bleaching and deodorizing said crude oil to produce the canola oil.

Another aspect of the present invention is to provide a method of producing a canola oil, comprising (a) crushing seeds produced by a *Brassica napus* plant which may be designated 04CWB930127, 04CWB930128, 04CWB930081, 04CWB930111, 04CWB930144, 04CWB930135, or 04CWB930015, representative seed being deposited under NCIMB accession no: 41395, 41396, 41393, 41394, 41398, 41397, or 41392, respectively, or may be a descendent of any said plants, wherein the plant or descendent plant is representative of a population having an SSDI % score which is less than about 60% of the SSDI % score of the variety Columbus, or of the variety Express, or of the mean score of the two varieties, under the same environmental and disease conditions in the field, (b) extracting a crude oil from said crushed seeds, and optionally (c) refining, bleaching and deodorizing said crude oil to produce the canola oil. Another aspect of the present invention is to provide a *Brassica napus* plant as discussed above, further having a level of blackleg (*Leptosphaeria maculans*) resistance greater than Pioneer Hi-Bred variety 46A76 under the same environmental and disease conditions in the field. The plant may be designated 03SN40341, 03SN40441, 02SN41269, 04DHS12921, 04DHS11319, or 04DHS11418, representative seed being deposited under ATCC accession no: PTA-6776, PTA-6779, PTA-6777, PTA-6781, PTA-6780, or PTA-6778, respectively, said seed deposited on or about Jun. 8, 2005; or may be designated 04SN41433, 04SN41415, 05DHS12897, or 04DHS12879, representative seed being deposited under NCIMB accession no 41389, 41388, 41391, or 41390, respectively; or may be a descendent of any said plants, wherein the plant or descendent plant is representative of a population having an SSDI % score which is less than about 60% of the SSDI % score of Pioneer Hi-Bred variety 46A76, or of Pioneer Hi-Bred variety 46A65, or of the mean score of the two varieties, under the same environmental and disease conditions in the field, and further has an average level of blackleg resistance greater than that of Pioneer Hi-Bred variety 46A76 under the same environmental and disease conditions in the field. Also provided is a plant cell from the plant.

BRIEF DESCRIPTION OF THE FIGURES

FIG. 2 shows agronomic and *Sclerotinia* data for specific *Sclerotinia*-resistant spring canola lines. *Sclerotinia* data are expressed as % of 46A76, 46A65 and their mean. Part A includes agronomic data and *Sclerotinia* data under extreme disease pressure field research conditions. Part B includes natural field data. Part C shows combined results of Part A and Part B. Part D is Part B with data of one natural field trial (NDSU 2005) omitted. Part E shows combined results of Part A and Part D.

DETAILED DESCRIPTION OF THE INVENTION

I. Overview

Figure 1A:
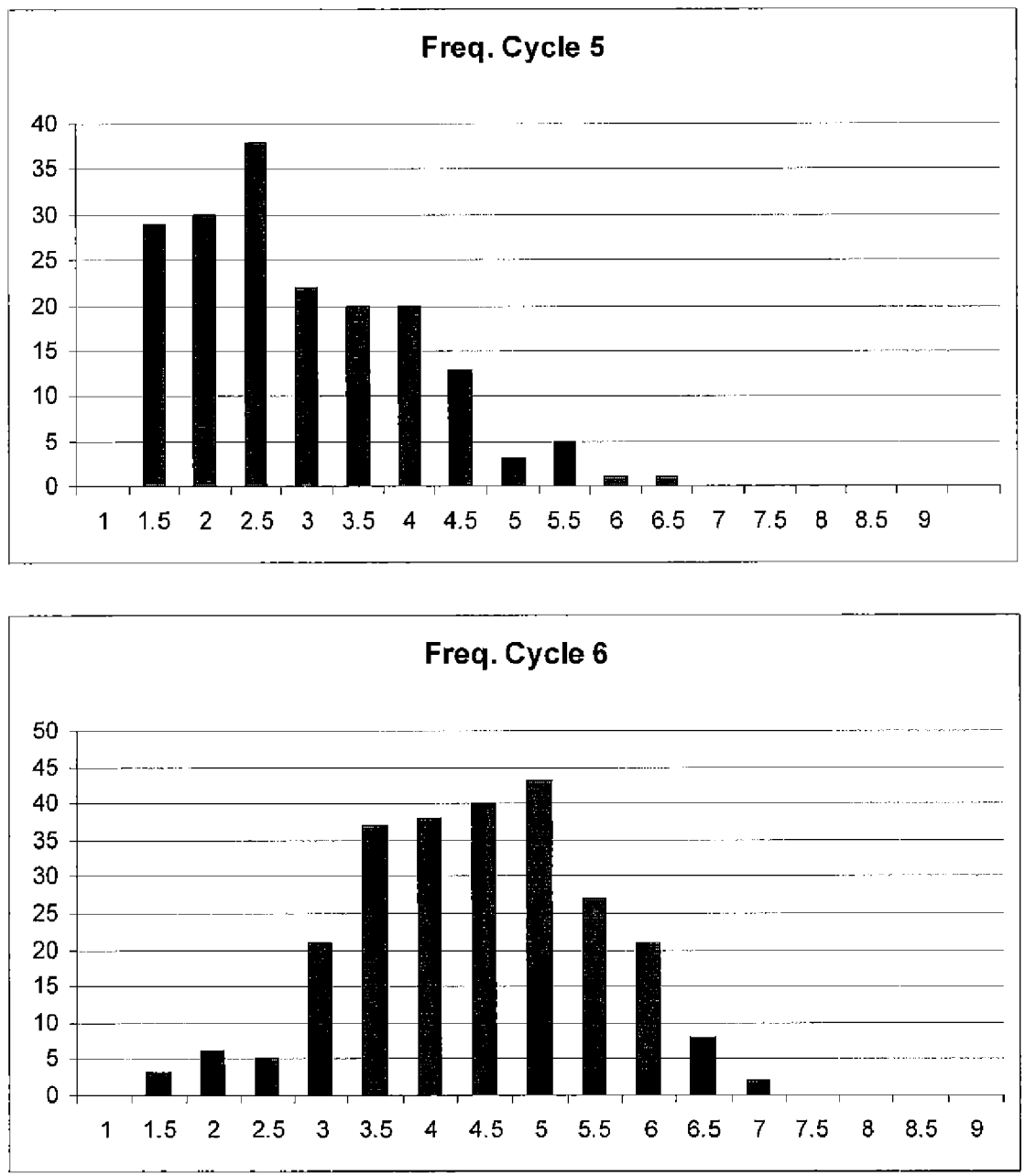
FIG. 1 is a histogram of cycles 5 to 10 of Population T from 2000-2005 under extreme disease pressure field research conditions. The Y-axis shows frequency of progenies. The X-axis shows the 1-9 SSDI *Sclerotinia* rating as described in Table 4.

The present invention discloses the first low erucic acid and low glucosinolate canola lines having a spring or winter habit and exhibiting high levels of field resistance to *Sclerotinia*. Field resistance is based on an accumulation of conventional partial physiological resistance to *Sclerotinia* in combination with morphological traits that function in synchrony to reduce disease development.

There are several aspects of this invention.

The first aspect is the development of *Sclerotinia* resistant canola lines. This aspect of the invention is described in examples 1, 2, 3, 4, 8 and 9. This is the first report of spring canola lines having an average level of *Sclerotinia* incidence of less than about 60% of the incidence level of Pioneer Hi-Bred variety 46A76, or of Pioneer Hi-Bred variety 46A65, or of the mean score of the two varieties under the same environmental and disease conditions in the field, as measured by the SSDI % score; or of winter canola lines having an average level of *Sclerotinia* incidence of less than about 60% of the incidence level of the variety Columbus, or the variety Express, or of the mean score of the two varieties under the same environmental and disease conditions in the field, as measured by the SSDI % score. The direct human technical intervention to genetically manipulate and pyramid multiple physiological and morphological traits during six years of breeding and selection efforts (2000-2005) stemming from 15 years of research (1991 to 2005) has resulted in spring canola lines with resistance to *Sclerotinia*. Seed deposits representing the improved lines have been made as detailed elsewhere herein, including Tables 11a and 11b.

The second aspect of the invention is developing canola lines with the combination of *Sclerotinia* resistance and blackleg resistance. The breeding and selection efforts described in examples 1, 2, 3 and 4 not only produced lines with *Sclerotinia* resistance, but also produced lines having blackleg resistance. The pyramiding of multiple physiological and morphological traits during six years of breeding and selection stemming from fifteen years of research resulted in lines with resistance to *Sclerotinia*, and also resistance to blackleg. This aspect of the invention is described in example 5.

The third aspect of the invention is the development of methodologies to screen for *Sclerotinia* resistance in the greenhouse or growth room and in the field. Development of these methodologies was one of the critical success factors in developing the *Sclerotinia*-resistant lines and backleg-resistant lines of the invention described in examples 1, 2, 3, 4 and 5. This aspect is described in examples 6 and 7.

II. Canola Breeding Techniques

Canola breeding programs utilize techniques such as mass and recurrent selection, backcrossing, pedigree breeding and doubled haploid development. For a general description of rapeseed and canola breeding, see, R. K. Downey and G. F. W. Rakow, 1987: Rapeseed and Mustard (In: Fehr, W. R. (ed.), Principles of Cultivar Development, 437-486. New York: Macmillan and Co.); Thompson, K. F., 1983: Breeding winter oilseed rape *Brassica napus*. Advances in Applied Biology 7:1-104; and Oilseed Rape, Ward, et al., Farming Press Ltd., Wharefedale Road, Ipswich, Suffolk (1985), each of which is hereby incorporated by reference.

A cross between two different homozygous lines produces a uniform population of hybrid plants (also called F1 hybrid plants) that may be heterozygous for many gene loci. A cross of two heterozygous plants that differ at a number of gene loci will produce a population of plants that differ genetically and will not be uniform. Regardless of parentage, plants that have been self-pollinated and selected for type for many generations become homozygous at almost all gene loci and produce a uniform population of true pureline progeny. The term "inbred" as used herein refers to a homozygous plant or a collection of homozygous plants. Those of ordinary skill will understand that some residual heterozygosity may exist in inbreds.

Choice of breeding or selection methods depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. In general, breeding starts with the crossing of two genotypes, each of which may have one or more desirable characteristics that is lacking in the other or which complements the other. If the two original parents do not provide all the desired characteristics, other sources can be included by making more crosses. In each successive filial generation, F1 to F2; F2 to F3; F3 to F4; F4 to F5, etc., plants are selfed to increase the homozygosity of the line. Typically in a breeding program five or more generations of selection and selfing are practiced to obtain a homozygous plant.

Pedigree breeding is commonly used for the improvement of self-pollinating crops. Two parents that possess favorable, complementary traits are crossed to produce an F1. An F2 population is produced by selfing one or several F1's or by sib-pollinating two F1's. Selection of the best individuals may begin in the F2 population; then, beginning in the F3, the best individuals in the best families are selected. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new varieties.

Backcross breeding has been used to transfer genes for simply inherited, highly heritable traits from a donor parent into a desirable, optimally homozygous, variety that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent plus the desirable trait or traits transferred from the donor parent. This approach has been used extensively for breeding disease-resistant varieties.

Each canola breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination and the number of hybrid offspring from each successful cross.

Mass selection and recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to the failure of some seeds to germinate or due to the failure of some plants to produce at least one seed. As a result, not all of the F2 plants originally sampled in the population will be represented by a progeny when generation advancement is completed.

In a multiple-seed procedure, canola breeders commonly harvest one or more pods, or siliques, from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed. If desired, the doubled haploid method can be used to extract homogeneous lines, thereby increasing the supply of seed with a desired genotype.

Molecular markers including techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPS) may be used in plant breeding methods. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles, or markers containing sequences within the actual alleles of interest, can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection or Marker Assisted Selection (MAS).

The production of doubled haploids (Swanson, et al., 1987) can also be used for the development of inbreds in the breeding program. After a cross is made, doubled haploid methods can be used to quickly obtain a homozygous plant. In *Brassica napus*, microspore culture technique is used in producing haploid embryos. The haploid embryos are then regenerated on appropriate media as haploid plantlets, doubling chromosomes of which results in doubled haploid plants. This can be advantageous because the process omits the generations of selfing needed to obtain a homozygous plant from a heterozygous source.

A pollination control system and effective transfer of pollen from one parent to the other offer improved plant breeding and an effective method for producing hybrid canola seed and plants. For example, the ogura cytoplasmic male sterility (cms) system, developed via protoplast fusion between radish (*Raphanus sativus*) and rapeseed (*Brassica napus*) is one of the most frequently used methods of hybrid production. It provides stable expression of the male sterility trait (Ogura, 1986), Pelletier, et al., (1983) and an effective nuclear restorer gene (Pellan-Dourme, et al., 1988).

In developing improved new *Brassica* hybrid varieties, breeders use self-incompatible (SI), cytoplasmic male sterile (CMS) and nuclear male sterile (NMS) *Brassica* plants as the female parent. In using these plants, breeders are attempting to improve the efficiency of seed production and the quality of the F1 hybrids and to reduce the breeding costs. When hybridization is conducted without using SI, CMS or NMS plants, it is more difficult to obtain and isolate the desired traits in the progeny (F1 generation) because the parents are capable of undergoing both cross-pollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of F1 hybrids includes crossing a CMS *Brassica* female parent with a pollen-producing male *Brassica* parent. To reproduce effectively, however, the male parent of the F1 hybrid must have a fertility restorer gene (Rf gene). The presence of a Rf gene means that the F1 generation will not be completely or partially sterile, so that either self-pollination or cross pollination may occur. Self pollination of the F1 generation to produce several subsequent generations is important to ensure that a desired trait is heritable and stable and that a new variety has been isolated.

An example of a *Brassica* plant which is cytoplasmic male sterile and used for breeding is ogura (OGU) cytoplasmic male sterile (Pellan-Delourme, et al., 1987). A fertility restorer for ogura cytoplasmic male sterile plants has been transferred from *Raphanus sativus* (radish) to *Brassica* by Instit. National de Recherche Agricole (INRA) in Rennes, France (Pelletier, et al., 1987). The restorer gene, Rf1 originating from radish, is described in WO 92/05251 and in Delourme, et al., (1991). Improved versions of this restorer have been developed. For example, see, WO98/27806 oilseed *Brassica* containing an improved fertility restorer gene for ogura cytoplasmic male sterility, which is hereby incorporated by reference.

Other sources and refinements of CMS sterility in canola include the Polima cytoplasmic male sterile plant, as well as those of U.S. Pat. No. 5,789,566, DNA sequence imparting cytoplasmic male sterility, mitochondrial genome, nuclear genome, mitochondria and plant containing said sequence and process for the preparation of hybrids; U.S. Pat. No. 5,973,233 Cytoplasmic male sterility system production canola hybrids; and WO97/02737 Cytoplasmic male sterility system producing canola hybrids; EP Patent Application Number 0 599042A Methods for introducing a fertility restorer gene and for producing F1 hybrids of *Brassica* plants thereby; U.S. Pat. No. 6,229,072 Cytoplasmic male sterility system production canola hybrids; U.S. Pat. No. 4,658,085 Hybridization using cytoplasmic male sterility, cytoplasmic herbicide tolerance, and herbicide tolerance from nuclear genes; all of which are incorporated herein.

Promising advanced breeding lines commonly are tested and compared to appropriate standards in environments representative of the commercial target area(s). The best lines are candidates for new commercial lines; and those still deficient in a few traits may be used as parents to produce new populations for further selection.

For most traits the true genotypic value may be masked by other confounding plant traits or environmental factors. One method for identifying a superior plant is to observe its performance relative to other experimental plants and to one or more widely grown standard lines. If a single observation is inconclusive, replicated observations provide a better estimate of the genetic worth.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which lines are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or is due to the environment or experimental error.

Proper testing should detect any major faults and establish the level of superiority or improvement over current lines. In addition to showing superior performance, there must be a demand for a new line that is compatible with industry standards or which creates a new market. The introduction of a new line commonly will incur additional costs to the seed producer, the grower, the processor and the consumer, for special advertising and marketing, altered seed and commercial production practices, and new product utilization. The testing preceding release of a new line should take into consideration research and development costs as well as technical superiority of the final line. For seed-propagated lines, it must be feasible to produce seed easily and economically. Preferably residual heterozygosity should not exceed 5%.

These processes, which lead to the final step of marketing and distribution, usually take approximately six to twelve years from the time the first cross is made. Therefore, the development of new lines such as that of the present invention is a time-consuming process that requires precise forward planning, efficient use of resources, and a minimum of changes in direction. Accordingly, significant technical human intervention is required.

Further, as a result of the advances in sterility systems, lines are developed that can be used as an open pollinated variety (i.e., a pureline cultivar sold to the grower for planting) and/or as a sterile inbred (female) used in the production of F1 hybrid seed. In the latter case, favorable combining ability with a restorer (male) would be desirable. The resulting hybrid seed would then be sold to the grower for planting.

Hybrid seed production of canola can be achieved using cytoplasmic male sterility. This type of hybrid production uses 3 inbred lines: a restorer line, an A line, and a B line. The restorer line, also called the R line, is used as the male in hybrid seed production. The restorer line has dominant nuclear genes, known as restorer genes, that are responsible for hybrid fertility. The R line is crossed to the A line to produce the F1 hybrid seed. The A line is male-sterile due to the cytoplasm and due to nonrestorer alleles in the nuclear genome. Because the A line is male sterile it cannot reproduce by itself. To reproduce the A line, a B line is developed. The B line, also called the maintainer line, is the genetic equivalent to the A line except that the B line has a normal cytoplasm and is therefore male fertile. The A line is pollinated by the B line. The seed developed on the A line plants is harvested and its progeny are crossed with the R line to produce the F1 hybrid seed.

The development of a canola hybrid in a canola plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in canola, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line per se, is a factor in the selection of improved canola lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, either through visual or molecular methods.

*Brassica napus* canola plants, without any male sterility or self incompatibility system, are recognized to commonly be self-fertile with approximately 70 to 90 percent of the seed normally forming as the result of self-pollination. The percentage of cross pollination may be further enhanced when populations of recognized insect pollinators at a given growing site are greater. Thus open pollination is often used in commercial canola production.

III. Definitions

Units, prefixes, and symbols may be denoted in their SI accepted form.

"Appropriate check", as used herein, means a *Brassica* genotype which provides a basis for evaluation of the *Sclerotinia* resistance of an experimental line. An appropriate check is grown under the same environmental conditions, including disease pressure, as is the experimental line, and is of approximately the same maturity as the experimental line. For example, for spring canola, an appropriate check is expected to mature within +/−10 days, usually +/−5 days, of the experimental line. Maturity standards are well known to one of skill in the art. An appropriate check is usually a widely-available or widely-grown variety. The term "appropriate check" may actually reflect multiple appropriate varieties. For example, for spring canola genotypes, each of Pioneer Hi-Bred varieties 46A76 and 46A65 is an appropriate check; the mean performance of the two varieties is also an appropriate check. For winter canola genotypes, each of public lines Columbus and Express is an appropriate check, as is the mean performance of the two varieties.

The term "canola" means a *Brassica* plant wherein the oil must contain less than 2% erucic acid and the solid component of the seed must contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil free solid.

The term "crossed" or "cross" in the context of this invention means the fusion of gametes via pollination to produce progeny (i.e., cells, seeds or plants). The term encompasses both sexual crosses (the pollination of one plant by another) and selfing (self-pollination, i.e., when the pollen and ovule are from the same plant).

The term "field capacity" means that the top 4 inches of soil, or approximately the top 4 inches of soil, are fully saturated with moisture, but with no or little standing water.

The term "field resistance" means a resistance measured under field conditions. It reflects the resistance of the entire plant or population of plants when exposed to the pest or pathogen in natural field conditions. Field resistance may be measured throughout the developmental stages of a plant, and may be expressed in terms of effect on harvestable yield, or may reflect a targeted evaluation during the growth stage when the plant is most susceptible to disease development.

The term "genetically linked" refers to genetic loci that are in linkage disequilibrium and statistically determined not to assort independently. Genetically linked loci assort dependently from 51% to 99% of the time or any whole number value there between, preferably at least 60%, 70%, 80%, 90%, 95% or 99%.

The term "inbred" as used herein refers to a homozygous plant or a collection of homozygous plants. Those of ordinary skill will understand that some residual heterozygosity may exist in inbreds.

The term "introgression" refers to the introduction of a desired genetic locus into at least one progeny plant via a sexual cross between parent plants and wherein at least one of the parent plants has the desired genetic locus within its genome.

The term "partial leaf resistance" means the extent of resistance to *Sclerotinia* on the leaf when compared to the leaf reaction on a susceptible plant. With partial leaf resistance, the disease develops more slowly on the plant, or to a lesser extent, than in a plant that is susceptible.

The term "marker" or "molecular marker" refers to a genetic locus used as a point of reference when identifying genetically linked loci such as a QTL (quantitative trait loci). The term also refers to nucleic acid sequences complementary to the genomic sequences, such as nucleic acids used as probes.

The term "partial stem resistance" or "stem resistance" means an incomplete resistance in the stem. It is the extent of resistance to *Sclerotinia* on the stem when compared to the stem reaction on a susceptible plant. In partial stem resistance the disease develops more slowly on the plant or to a lesser extent than in a plant that is susceptible. However, in a plant that has "partial stem resistance", the plant becomes diseased (compare with complete resistance).

The term "complete resistance" means a resistant reaction in which an aspect of disease development, usually symptom expression or pathogen reproduction, is completely stopped (compare with partial resistance).

The term "recurrent selection" means a breeding system with the objective of increasing the frequency of favorable genes of a quantitatively inherited characteristic by repeated hybridization and cycles of selection.

The term "maturity" or "days to maturity" means the number of days from seeding to harvest. Maturity will vary considerably between and within genotypes, depending on location, growing season and date of seeding.

The term "population" as used herein means an interbreeding group of plants or a group of individuals that share a common gene pool. A population may be homogenous (genetically uniform), such as an F1 population created by crossing homozygous parents; or genetically diverse, such as the segregating progeny of a population created by selfing a heterozygous plant or by crossing heterozygous parents. Further, a homogenous population may be bred to be homozygous at almost all gene loci and produce a uniform population of true pureline progeny.

The term "population breeding" refers to improvement in a population carried through breeding while using the individuals from the same population as parents. Population breeding can mean performing recurrent selection within a population.

The term "spring *Brassica*" or "spring canola" means a *Brassica* plant that does not have a vernalization requirement.

The term "*Sclerotinia* conducive morphology" or "*Sclerotinia* conducive phenotype" means a *Brassica* phenotype in which *Sclerotinia* infection can establish and develop more easily compared to a *Brassica* phenotype that is less conducive to *Sclerotinia* infection. For example, a *Sclerotinia* conducive morphology may include at least one of the following morphological traits: tight branching, low branching, extended duration of flowering, high petal retention, high degree of leaf retention, and a propensity to lodge or lean. These morphological traits provide a good source of the initial inoculum from the petals and increase moisture surrounding the plant. In contrast, plants exemplifying morphological traits that are less conducive to *Sclerotinia* infection may include at least one of the following traits: low petal retention, petal-less phenotype, good standability, less compact branching, high branching, and early leaf abscission. These morphological traits decrease inoculum from the petals as well as the level of moisture surrounding the plant.

The term "disease incidence" means the number of plants affected by a disease within a sample. It is typically presented as the percentage of plants affected by the disease with respect to the total number of plants in the sample.

The term "SSDI %" means percentage *Sclerotinia Sclerotiorum* Disease Incidence and is measured as the percentage of plants in a population infected with *Sclerotinia sclerotiorum*.

The term "SSDI" means a rating from 1 to 9 and measures the *Sclerotinia Sclerotiorum* Disease Incidence under controlled extreme disease pressure field research conditions as described in Example 7 and Table 4. SSDI measures the percentage of plants in a population that are infected with *Sclerotinia sclerotiorum* as compared to an appropriate check variety. For spring canola an appropriate check is Pioneer Hi-Bred variety 46A76 and/or Pioneer Hi-Bred variety 46A65. For winter canola an appropriate check is Columbus and/or Express. For example, for spring canola, 5 rows of test lines are sown between one row of Pioneer Hi-Bred variety 46A76 on one side and Pioneer Hi-Bred variety 46A65 on the other. Typically, under extreme disease conditions, Pioneer Hi-Bred variety 46A76 has a disease incidence of 60% (SSDI %) and 46A65 has a disease incidence of 70% (SSDI %), for an average of 65% (SSDI %). If in any particular test plot, the SSDI % average of Pioneer Hi-Bred variety 46A65 and Pioneer Hi-Bred variety 46A76 was not 65%, the scores of Pioneer Hi-Bred variety 46A65 and Pioneer Hi-Bred variety 46A76 would be multiplied by a factor to bring them to an average of 65%. The scores of the test lines would also be multiplied by this factor. The lines would then be given the rating that corresponds with the SSDI % as found on Table 4. For example, if the mean of checks is 70%, a factor 65/70 would be used to decrease the percentage disease incidence measured on the experimental lines growing between the checks because of higher-than-targeted disease pressure. Conversely, if the mean is 60%, a factor 65/60 would be used to accordingly increase (adjust) SSDI % on the experimental lines because of the lower-than-targeted disease pressure. Although targeted disease incidence is 65%, variation around the target is expected due to the large sample of plants, environmental variation and variation in inoculum, therefore adjustments via checks enables comparison of lines within the nursery and prevents misclassification of the field reaction. Extreme disease pressure field research conditions as described in Example 7 were used extensively to produce the *Sclerotinia* resistant lines of the invention because conditions favorable for *Sclerotinia* do not occur in a predictable fashion in nature. Therefore in an effort to expedite selections and to provide reproducible conditions, extreme disease pressure field research conditions were used.

The SSDI rating for trials, after adjustment for incidence, is further adjusted by taking into account the severity of the disease. Therefore, after adjusting the SSDI % as previously explained, SSDS adjustments are made as well. The mean SSDS on infected plants of checks (scores of 1-8) is compared with that of the experimental entry. If the mean SSDS score was better on the experimental line (for example a rating of 3 on the checks versus 4 on the experimental line) the SSDI % was adjusted by multiplying by ¾. For example, if the SSDI % of the experimental line was 20%, ¾ multiplied by 20%=15%. This corresponds to a rating of 7.5 on the SSDI scale. Conversely, if the SSDS on the experimental entry was 2 (more affected) versus 3 on the checks, the SSDI % would be multiplied by 3/2. For example, if the SSDI % was 20%, multiplied by 3/2 would equal 30%. This corresponds to a rating of 6.0 on the SSDI scale.

The term 'extreme disease pressure field research conditions' means controlled disease research conditions as described in Example 7. For example, extreme disease pressure is generated with the application of Niger seed carrier mimicking *Sclerotinia*-colonized petals. Natural inoculum may be present in the field as a backup inoculum. The percent disease incidence of the test plants are adjusted to running checks as described above, and given an SSDI score of 1 to 9. However, under these extreme conditions plants are more susceptible to *Sclerotinia* for at least the following reasons: (1) under extreme disease pressure field research conditions, the plants are subjected to wetness provided by misting irrigation which is favorable for *Sclerotinia* development, (2) under extreme disease pressure field research conditions the plants are in a semi-enclosed environment due to the artificial canopy which ensures continuous moist conditions favorable for *Sclerotinia* development, and (3) under extreme disease pressure field research conditions there are six rows of different test plants in each plot, therefore any one row of test plants having a particular morphological phenotype may be surrounded by two different rows of plants with different morphological phenotypes. Accordingly, any benefits from a morphological phenotype that is less conducive to *Sclerotinia* infection (for example high branching) are decreased because any one row may be surrounded by plants having a different morphological phenotype (for example low branching). In contrast, a plant growing under natural field conditions is (1) not enclosed in an artificial canopy which ensures continuous moisture and (2) is grown in plots surrounded by plants with the same morphological phenotype which allows all benefits from the morphology to be expressed. Accordingly, selections having a morphology that is less conducive to *Sclerotinia* infection, for example high branching, perform significantly better under natural field conditions compared to extreme disease pressure field research conditions.

The term 'natural field disease conditions' means conditions in yield plots in irrigated or non-irrigated fields. Infection is attained via mycelium from colonized petals. Yield plots provide a sample of the plant population that reflects natural conditions similar to farmers' fields. SSDI % is used to express the percentage of infected plants in replicated trials. In addition to SSDI %, data on individual plants can be collected to reflect severity (SSDS) on different scales (1-9 Pioneer scale and 0-5 Public scale). Other parameters that further quantify the impact of disease, for example *Sclerotinia sclerotiorum* Field Severity (SSFS), as described below and shown in Table 2, can also be evaluated. SSFS can be informative especially under high natural field disease pressure.

The term "disease severity" means the extent of damage to a plant resulting from infection by a pathogen. There are two scales used in this invention to measure disease severity. The first is the Pioneer Hi-Bred scale from 1 to 9. The second is the scale used by researchers in public institutions and is referred to as the Public scale from 0-5. Both are described in Table 15. Some examples of their use are presented in Table 2.

The term "SSDS" means *Sclerotinia Sclerotiorum* Disease Severity and is a measurement of the extent of disease development on an infected plant. For example, it distinguishes between plants with minor symptoms versus dead plants. For the purposes of this invention, two rating scales are used: (1) The Pioneer SSDS rating scale ranges from 1 to 9 and is described in Table 15; and (2) The Public Scientists' scale ranges from 0 to 5 and is described in the footnote in Table 2.

The term "SSFS" means *Sclerotinia Sclerotiorum* Field Severity and is a measurement of the product of disease incidence (SSDI %) and the extent to which infected plants were diseased under natural field conditions (SSDS). It is a measure of the fungal impact in the field and can be more informative under high disease pressure, i.e. when disease incidence becomes significant in the field. It is calculated by multiplying the SSDI % by the disease severity and dividing by 5, wherein the disease severity is rated 0 to 5, with 0 being no infection and 5 being a dead plant as described in Table 2.

The term "quantitative trait locus" or "QTL" refers to segregating genetic factors that affect the variability in expression of a phenotypic trait.

TABLE 2

Field-collected *Sclerotinia* parameters SSDI % and SSDS and their relationship to derived parameters SSDI (research data) and SSFS (natural data).

| Trait | SSDI % Disease Incidence | SSDS Disease severity of affected plants | SSDI Based on adjusted SSDI % under extreme disease pressure field research conditions | SSFS Field severity based on both SSDI % and SSDS used in natural field conditions |
|---|---|---|---|---|
| Scale | 0-100% | Pioneer SSDS scale 1 = dead 9 = no disease Public scale 0 = no disease 5 = dead plant | 1-9 Conversion of SSDI % and adjustment for checks | 0-100% % field impact - quantifies damage in the field irrespective of disease pressure |
| Usage Adjustments | General N/A | General N/A | Pioneer only Adjusted to checks | General Unadjusted |
| Examples: Different combinations of disease incidence and disease severity | | Pioneer SSDS scale | Public scale | | |
| Example 1 | 80 | 1 | 5.0 | 1.0 (80) | 80 |
| Example 2 | 80 | 5 | 2.0 | 2.6 (64) | 32 |
| Example 3 | 50 | 5 | 2.00 | 5.0 (40) | 20 |
| Example 4 | 30 | 7 | 1.0 | 7.3 (17) | 6 |
| Example 5 | 10 | 8 | 1.0 | 8.5 (5) | 2 |

SSDI % is the percentage of plants in a population infected with *Sclerotinia*.

SSDS is a rating of the extent of disease development on an affected plant. Two scales are used in the invention. The Pioneer SSDS scale ranges from 1 (dead) to 9 (no disease) and the Public scale ranges from 0 (no disease) to 5 (dead) plant. For details of the Pioneer SSDS scale, see Table 15. The Public scale is provided as follows: 0=no disease; 1=superficial lesions or small branch affected; 2=large branch dead; 3=main stem at least 50% girdled; 4=main stem girdled but plant produced good seed; 5=main stem girdled, much reduced yield.

SSDI is a rating of 1 to 9 as described on Table 4, and adjusted to the SSDI % of the check varieties 46A65 and/or 46A76 for spring canola, and check varieties Express and/or Columbus for winter canola. This rating is used only under controlled extreme disease pressure field research conditions. It is calculated by multiplying the observed SSDI % by Factor X, where Factor X is the factor that brings the average SSDI % of the appropriate checks to 65%. Adjustment for severity is done after incidence adjustment. The SSDI is then calculated according to the scale on Table 4. For examples 1 to 5, assumptions are that mean SSDI % on checks=65% and the mean SSDS on checks=4 to calculate SSDI values.

SSFS is a measure of both disease incidence and severity under natural disease pressure in the field. It is calculated as follows: SSFS=[SSDI %×SSDS (0-5 scale)]÷5

IV. EXAMPLES

*Sclerotinia* stem rot develops in canola via colonized petals in extended moist conditions at flowering. Dropped petals enable *Sclerotinia* to infect leaves of canola leading towards the stems. The fungus causes *Sclerotinia* stem rot. The plant dies prematurely which results in a yield loss of approximately 50%.

Canola is susceptible to *Sclerotinia* stem rot. In years with extended wet periods, damage to canola can be very significant. To reduce or prevent that damage, farmers generally apply one or two fungicide applications, depending on the duration of the wet period.

Example 1

Determining the Performance of Canola Checks Under Low, Moderate, High, Very High and Extreme Disease Field Research Conditions Methods and Materials In an effort to determine the level of *Sclerotinia* tolerance in currently available spring canola cultivars under low, moderate, high and very high *Sclerotinia* conditions, data was collected from natural field conditions over many years, including public yield plots. The data is summarized in Table 3. Data for 44A89 and 46A65 came from a five replication-natural trial in Minnesota in 2001 (Jurke and Fernando, 2003). The data for Pioneer Hi-Bred variety 46A76 is an estimate based on the reaction of similar entries in the same Minnesota trial as well as North Dakota data from 2003. The data for the performance of the canola checks under extreme disease conditions was generated in this study.

Winter canola lines Columbus and Express were included in extreme disease pressure research trials as running checks. As shown in Table 4 and Table 10c, these are susceptible or moderately susceptible lines.

Extreme disease conditions are rare but may occur, and the goal was to screen lines under such conditions. Extreme disease pressure occurs with 20-30 days of continuous wetness and temperatures averaging 20 to 25° C. Plants infected with *Sclerotinia* under extreme conditions usually require two fungicide applications to withstand the disease. On average, fungicides provide 10-14 days of protection per application. Screening selections under extreme conditions ensures the selections can withstand typical disease pressure.

Because extreme disease conditions occur rarely in nature, artificial extreme conditions were generated in the field as described in Example 7. This included artificial inoculum in the form of *Sclerotinia*-colonized Niger seed, the use of irrigation, and the use of a netting to maintain a moist environment. Pioneer Hi-Bred varieties 44A89, 46A65 and 46A76 were tested. Less susceptible 46A65 and 46A76 were used as running checks to monitor disease levels and determine performance (SSDI).

In an effort to determine the effect of fungicide spraying on *Sclerotinia*-infected fields, data from yield plots under natural field conditions and inoculum, and sprayed with Lance™ fungicide during 30% flowering, was collected and summarized.

Results

Table 3 shows the performance of spring canola checks under various conditions. Screening for disease incidence (i.e., the percentage of plants infected with *Sclerotinia*) was the primary goal.

Previous field data indicated that typical moderate or high field disease pressure results in 20-50% disease incidence on 46A65 and 10-40% disease incidence on 46A76 (Table 3). However, under extreme conditions as shown in Table 3, the percentage of disease incidence on Pioneer Hi-Bred variety 46A65 is approximately 70% and the percentage of disease incidence on Pioneer Hi-Bred variety 46A76 is 60%. If the weather becomes unfavorable for *Sclerotinia* infection, the canola checks are less affected and the disease incidence on partially resistant materials is proportionally minimized or eliminated. Since most field situations are based on less than extreme disease pressure, the checks and the developed lines will normally be less affected than shown in Table 4.

Screening for disease incidence under extreme disease pressure and against running checks every six rows under misting irrigation, was also done as described in Example 7. This extreme disease pressure research field data is presented as an SSDI rating of 1 to 9 on Table 4. Typically, 5 rows of test lines were sown between one row of Pioneer Hi-Bred variety 46A76 on one side and one row of Pioneer Hi-Bred variety 46A65 on the other. Under extreme disease conditions, Pioneer Hi-Bred variety 46A76 has a disease incidence of 60% (SSDI %) and Pioneer Hi-Bred variety 46A65 has a disease incidence of 70% (SSDI %), for an average of 65% (SSDI %). If in any particular test plot, the SSDI % average of Pioneer Hi-Bred varieties 46A65 and 46A76 was not 65%, the scores of Pioneer Hi-Bred variety 46A65 and Pioneer Hi-Bred variety 46A76 would be multiplied by a factor to bring them to an average of 65%. The scores of the test lines would also be multiplied by this factor. After making the severity adjustment as described in the definition of SSDI, the lines would then be given the rating that corresponds with the SSDI as found on Table 4.

TABLE 3

Variation in natural *Sclerotinia* field reaction of currently available spring canola (SSDI %)

| Category | Variety | Disease Pressure | | | | |
| --- | --- | --- | --- | --- | --- | --- |
| | | Low | Moderate | High | Very High | Extreme* |
| Highly susceptible | 44A89 | 10-30 | 30-60 | 50-80 | 70-90 | 80-100 |
| Susceptible | 46A65 | 0-10 | 20-30 | 30-50 | 40-60 | 70 |
| Moderately susceptible | 46A76 | 0-10 | 10-20 | 20-40 | 30-50 | 60 |
| % of occurrence - field** | | 40 | 30 | 20 | 8-9 | 1-2 |

*Extreme disease pressure is used for core research and development as described in Example 7.
**Estimate of frequency of each infection level in farmers' fields in Western Canada, North Dakota and Minnesota.

TABLE 4

Measuring field performance under extreme disease pressure (research trials)

| Rating SSDI** | Category | Disease incidence SSDI % | Spring Checks | Winter Checks |
| --- | --- | --- | --- | --- |
| 1.0 | Highly susceptible | ≧80 | 44A89, Westar | Panther |
| 1.1-2.0 | Susceptible | 79-70 | 46A65 = 2 | Columbus = 2 |
| 2.1-3.0 | Moderately susceptible | 69-60 | 46A76 = 3 | Express = 3 |
| 3.1-4.0 | | 59-50 | | |
| 4.1-5.0 | Moderately resistant | 49-40 | | |
| 5.1-6.0 | | 39-30 | | |
| 6.1-7.0 | Resistant | 29-20 | | |
| 7.1-8.0 | | 19-10 | | |
| 8.1-9.0 | Highly resistant | 9-0 | | |

*SSDI % *Sclerotinia Sclerotiorum* Disease Incidence %
**SSDI *Sclerotinia Sclerotiorum* Disease Incidence rating as adjusted for incidence and severity on checks 46A65/46A76 for spring canola and Express/Columbus for winter canola under extreme disease pressure (research trials).

Table 5 shows that fungicide applications reduce the effect of *Sclerotinia* on *Brassica* and can be used as an indirect measure of improvements in performance against *Sclerotinia*. Table 5 shows the effect of one fungicide application in replicated yield plots under natural infection at Morden and Carman, Manitoba in 2004. As seen in Table 5, under conditions of lower disease pressure, near-complete control of *Sclerotinia* is achieved with a single fungicide application, except for highly susceptible materials. Fungicide efficacy on material with a rating of 1 (HS) is lower than the fungicide efficacy on material rated 2 or 3 (S or MS).

TABLE 5

*Sclerotinia* infection (SSDI %) on sprayed* and unsprayed checks in yield plots under natural conditions-in Morden, Manitoba and Carman, Manitoba locations in 2004

| Variety | Category | Morden | Carman | Mean | Fungicide application |
| --- | --- | --- | --- | --- | --- |
| 44A89 | HS | 30.7 | 22.5 | 27 | Unsprayed |
| 44A89 | HS | 8.0 | 19.5 | 14 | Sprayed |
| 46A65 | S | 11.3 | 11.5 | 11 | Unsprayed |
| 46A65 | S | 0.0 | 2.0 | 1 | Sprayed |
| 46A76 | MS | 11.3 | 9.5 | 10 | Unsprayed |
| 46A76 | MS | 2.7 | 1.0 | 2 | Sprayed |

*Lance ™ (boscalid) - BASF registered fungicide for control of *Sclerotinia*
HS = highly susceptible;
S = susceptible;
MS = moderately susceptible Table 6 shows the results from the field trials in North Dakota/Minnesota conducted in 2003. Most currently commercially available canola varieties are rated 1 or 2 based on Pioneer's SSDI rating of 1 to 9 as described in Table 2. Some rare varieties are rated 3 and are more effectively protected by fungicides. For example, Table 6 shows that Hyola 357, having a *Sclerotinia* rating of approximately 2, had 69% incidence in the North Dakota fungicide trials. After application of the best fungicide, the incidence was reduced to 44%. Table 6 also shows that Invigor2663, having a *Sclerotinia* rating of 1 to 2, had 22.3% incidence in the Minnesota trial, where disease pressure was low. After application of the fungicide, the incidence was reduced to 5%.

TABLE 6

Canola variety performance in the *Sclerotinia* screening and fungicide trials at same locations, North Dakota State University Carrington Research/Extension Center and University of Minnesota Red Lake Falls, 2003.*

| | North Dakota | | | Minnesota | | |
| --- | --- | --- | --- | --- | --- | --- |
| Variety | Disease Incidence | Disease Severity | Field Severity | Disease Incidence | Disease Severity | Field Severity |
| Hyola 357-untreated fungicide trial | 69 | 2.3 | 32.1 | | | |
| Hyola 357-treated fungicide trial Endura(Boscalid) | 44.0 | 1.9 | 16.6 | | | |
| Hyola 357-variety trial | 60.5 | 2.6 | 30.9 | 18 | 4.8 | 17.3 |
| InVigor2663-variety trial | 61.5 | 2.8 | 34.4 | 30.0 | 4.5 | 27.0 |
| InVigor2663-untreated fungicide trial | | | | 22.3 | 4.0 | 17.9 |

TABLE 6-continued

Canola variety performance in the *Sclerotinia* screening and fungicide trials at same locations, North Dakota State University Carrington Research/Extension Center and University of Minnesota Red Lake Falls, 2003.*

| Variety | North Dakota | | | Minnesota | | |
|---|---|---|---|---|---|---|
| | Disease Incidence | Disease Severity | Field Severity | Disease Incidence | Disease Severity | Field Severity |
| InVigor2663-treated fungicide trial Endura(Boscalid) | | | | 5.0 | 3.3 | 3.1 |

Based on disease incidence and Table 3, the North Dakota trial can be classified as very high to extreme disease pressure. Outcome of the fungicide trial at North Dakota is comparable with extreme disease pressure on the Pioneer SSDI scale of 1-9 and indicates performance of best fungicide in protection of a susceptible variety. Endura ™ (Boscalid ™) provided the highest level of the protection in the trial against a number of other fungicides under this pressure.
*From 2003 Evaluations for fungicides for Control of *Sclerotinia* Stem Rot of Canola in North Dakota and Minnesota, NDSU Extension Service April 2004.

Example 2

Developing Resistance to *Sclerotinia*-Population T Development

The target of the research effort was to replace fungicide treatment of canola with *Sclerotinia*-resistant varieties. The strategy was to use naturally available sources with partial resistance and pyramid these with disease-avoiding morphological traits through recurrent selection within a population, in order to attain a very high level of partial resistance. Once pyramided in a disease-avoiding background, resistance would be complete if it were built to sustain the maximum length of exposure to the disease, starting from petal drop to the end of flowering, and therefore would withstand the pathogen without significant damage to the plant.

Disease-avoiding morphological traits include, for example, good standability and stiff stalk (stem), later maturity, high branching, lower petal retention and rapid leaf abscission. Physiological traits are primarily strong partial stem resistance which may be associated with some leaf resistance. Thus, disease development which is reduced by morphological traits is further reduced where stem and/or leaf resistance is present. The overall impact of the fungus on the stem is decreased or minimized when a strong partial resistance in stems is combined with morphological traits that reduce the impact of the disease. In the absence of favorable morphological traits, overall performance is reduced but still significantly better than canola checks.

Extreme disease pressure occurs with prolonged periods of favorable weather conditions for *Sclerotinia* infection. Typically, this occurs with temperatures between 20 and 25° C. and relative humidity of greater than 80%. Under these conditions, optimal plant infection occurs (Heran, et al., 1999). In addition to humidity, another indicator of wet plant canopy is free moisture or absolute moisture on plants.

Methods and Materials

Tables 7 and 8 describe the components used in developing field resistance in Population T and the methods used to develop and screen for field resistance.

Starting in 1986, *Brassica napus* rapeseed germplasm from government agencies in the United States (United States Department of Agriculture), Japan (Ministry of Fishery and Natural Resources) and Canada (Plant Genetic Resources) was acquired. Rapeseed is high in glucosinolates and erucic acid and therefore is not canola quality. It is referred to as double high. In contrast, *Brassica napus* canola quality is low in erucic acid and low in glucosinolates and is also referred to as double low. It is defined as a *Brassica* plant wherein the oil must contain less than 2% erucic acid and the solid component of the seed must contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil free solid.

The acquired rapeseed germplasm was characterized for stem reaction to *Sclerotinia* (Table 7). A number of partially stem resistant rapeseed selections were crossed with canola quality lines, and progenies with partial stem resistance and canola quality traits (low erucic and/or low glucosinolates) were extracted. Canola quality lines that exhibited partial stem resistance were used for further research and population development. The sources of *Sclerotinia* resistance used in development of improved spring canola lines are listed in Table 7. Introductions from the USDA (US) and MAFF (Japan) were also used in development of improved winter canola lines.

In 1991, Pioneer started a population breeding program to recombine canola materials with physiological partial stem resistance and field morphological avoidance. Population T was assembled. Details of Cycles 0 to 10 are shown in Table 8. Each cycle is described in a row in the table. Each row describes the material used, intercrossing to generate $S_0$, seed increases and greenhouse selection on $S_0$ to generate $S_1$, followed by $S_1$ testing in the field and selection including agronomy and quality analysis. The first four cycles employed a closed population as described in Table 8. Further variability for physiological partial stem resistance was injected into Cycles 5, 6, 7 and 8 (Table 8). The lines were tested following the greenhouse and field methods of selection as described in Examples 6 and 7. Progenies exhibiting high levels of resistance were extracted and continuous improvement was observed in the field (FIG. 1). Following the method of Example 6, only greenhouse stem-selected progenies were advanced to the field.

TABLE 7

Population T development - Rapeseed components that were converted to canola and used in the development of Population T (Indoor Stem Lesion length and SSDS data on original lines or their spring selections (USDA) vs. susceptible checks)

| Institution | Rapeseed source variety name | Receiving year | Introgressing year | Lesion Length Millimeter | SSDS 1-9 | Lesion Length Susceptible Check | SSDS 1-9 Susceptible Check |
|---|---|---|---|---|---|---|---|
| The Ministry of Agriculture, Forestry and Fisheries of Japan MAFF | JAP 3-1-1 | 1988 | 1991 | 33 | 4.4 | 72* | 2.0 |
| | Ro (USSR) 6 | 1988 | 1991 | 28 | 4.2 | 48 | 1.0 |
| | Genkai | 1988 | 1999 | 60 | 1.4 | 72 | 2.0 |
| | Minami kyuushuu 17 | 1988 | 2000 | 10 | 5.4 | 48 | 1.0 |
| USDA North Central Regional Plant Introduction Station Iowa State University | PI470079 | 1988 | 2001 | 32 | 4.7 | 109** | 1.1 |
| | PI469955 | 1988 | 2001 | 27 | 4.5 | 120 | 1.0 |
| | PI469830 | 1988 | 2002 | 35 | 5.0 | 104 | 1.0 |
| Plant Genetic Resources Canada | PGR 8487 | 1986 | 2002 | 27 | 5.2 | 85 | 1.2 |
| | PGR 8488 | 1986 | 2002 | 32 | 4.8 | 85 | 1.2 |
| | PGR 8490 | 1986 | 2002 | 33 | 4.1 | 85 | 1.2 |
| | PGR 8492 | 1986 | 2002 | 34 | 4.6 | 85 | 1.2 |
| | PGR 8493 | 1986 | 2002 | 23 | 6.3 | 85 | 1.2 |

*Susceptible check for Japanese material spring canola Westar
**Susceptible check for USDA and PGR materials was Pioneer's spring line NS1602

TABLE 8

Population T development through S1 recurrent selection method with modifications.

| POPULATION POP T | MATERIAL Partially Resistant SOURCE | Crossing selections Intercross for $S_0$ | $S_0$ to $S_1$ Grow GH Test Select $S_0$ to $S_1$ | $S_1$ Characterization Field Test $S_1$ From selected $S_0$ Sclerotinia | Year | Type of the test Disease pressure | Field Checks | Comments Additional Selection at S1 Agronomy and Quality Analysis |
|---|---|---|---|---|---|---|---|---|
| CYCLE 0 ESTABLISHING population | JAP 3-1-1 Ro (USSR) 6 | 12 lines Twice Half diallel | 500 | GH Stem inoculation 500 | 1993-1995 | Stem test | | |
| CYCLE 1 | Closed Population | 33 $S_1$ lines | 500 | 150 | 1996 | Natural Moderate to high Pressure | NS1602 NS1604 Not running | $S_1$ NIR selection Low glucosinolates |
| CYCLE 2 | Closed Population | 30 $S_1$ Lines | 500 | 90 | 1997 | Moderate Pressure | 46A65 NS1604 Pairs of checks | $S_1$ NIR selection Low glucosinolates |
| CYCLE 3 | Closed Population | 12 $S_1$ Lines | 500 | 150 | 1998 | Moderate Pressure | 46A65 NS1604 Pairs of checks | $S_1$ NIR selection Low glucosinolates |
| CYCLE 4 | Closed Population | 15 $S_1$ Lines | 3,000 | 1,100 unreplicated | 1999 | Extreme | 46A65 NS1604 | $S_1$ NIR selection Low glucosinolates |
| CYCLE 5 | Open population BC1 GENKAI | 62 $S_1$s + 15 Genkai lines | 3,000 | 176 | 2000 | Extreme 2 reps | 46A65 NS1604 | $S_1$ Agronomic NIR selection Low glucosinolates |
| CYCLE 6 | Open Population BC1 MINAMI KYUUSHUU 17 | 41 C5 + 9 F1 introgressions | 3,000 | 150 | 2001 | Extreme 2 reps | 46A65 46A76 | $S_1$ Agronomic NIR selection Low glucosinolates Blackleg selection |

TABLE 8-continued

Population T development through S1 recurrent selection method with modifications.

| POPULATION POP T | MATERIAL Partially Resistant SOURCE | Crossing selections Intercross for $S_0$ | $S_0$ to $S_1$ Grow GH Test Select $S_0$ to $S_1$ | $S_1$ Characterization Field Test $S_1$ From selected $S_0$ Sclerotinia | Year | Type of the test Disease pressure | Field Checks | Comments Additional Selection at S1 Agronomy and Quality Analysis |
|---|---|---|---|---|---|---|---|---|
| Cycle 7 | Open Population BC1 PI469955 PI470079 | 24 $S_1$s cross with F1 introgression | 3,000 | 600 | 2002 | Extreme 2 reps | 46A65 46A76 | $S_1$ Agronomic NIR selection Low glucosinolates |
| Cycle 8 | Open Population BC0 PGR8487 PGR8488 PGR8490 PGR8492 PGR8493 PI469830 | 30 $S_1$ | 4,000 | 600 | 2003 | Extreme 2 reps | 46A65 46A76 | $S_1$ Agronomic NIR selection Low glucosinolates |
| Cycle 9 | Closed Population | 24 $S_1$s | 4,000 | 600 | 2004 | Extreme 2 reps | 46A65 46A76 | $S_1$ Agronomic NIR selection Low glucosinolates |
| Cycle 10 | Closed Population | 62 S1s | 4,000 | 390 | 2005 | Extreme 2 reps | 46A65 46A76 | S1 Agronomic NIR selection |

Table 8 Notes:
Replicated testing occurred since Cycle 6.
"Material" includes genetic backgrounds used in development of source materials of canola quality
Closed Population = Population development based only on progenies from previous cycle, no new sources introduced
Open population = Population development based on progenies from the previous cycle as well as new sources previously not present in the population.
Introgression = Introduction of a new source into the population; associated with open population
GH = greenhouse
The letter F is usually used in breeding (in pedigree breeding) and represents filial/progeny generation, F1 being first-generation seed or plant from the cross.
S refers to selfing, F1 is S0 or no selfing. In this way one can differentiate progenies from population (S) vs pedigree breeding (F).
S0 is F1 and is often used in population breeding to indicate a number of selfing generations
S1 in population breeding is equivalent to F2 in pedigree breeding
Examples of different approaches as follows:
Year 0 Intercrossing source material to produce S0, S0 Selfing/selecting, S1 field selection in closed population
Year 1 Intercrossing of S1s to produce S0, S0 Selfing/selecting, S1 field selection; example of closed Cycle (Cycles 1-4 and Cycle 9, 10)
Year 2 Intercrossing of S1 from Year 1 and new sources - BC0 approach (Cycle 8) or example of open cycle (Cycle 8) Intercrossing of S1 from Year 1 and new sources already crossed with Pop T - BC1 approach (Cycles 5, 6, 7); example of open cycle (Cycles 5, 6, 7)

Results

Figure 1B:
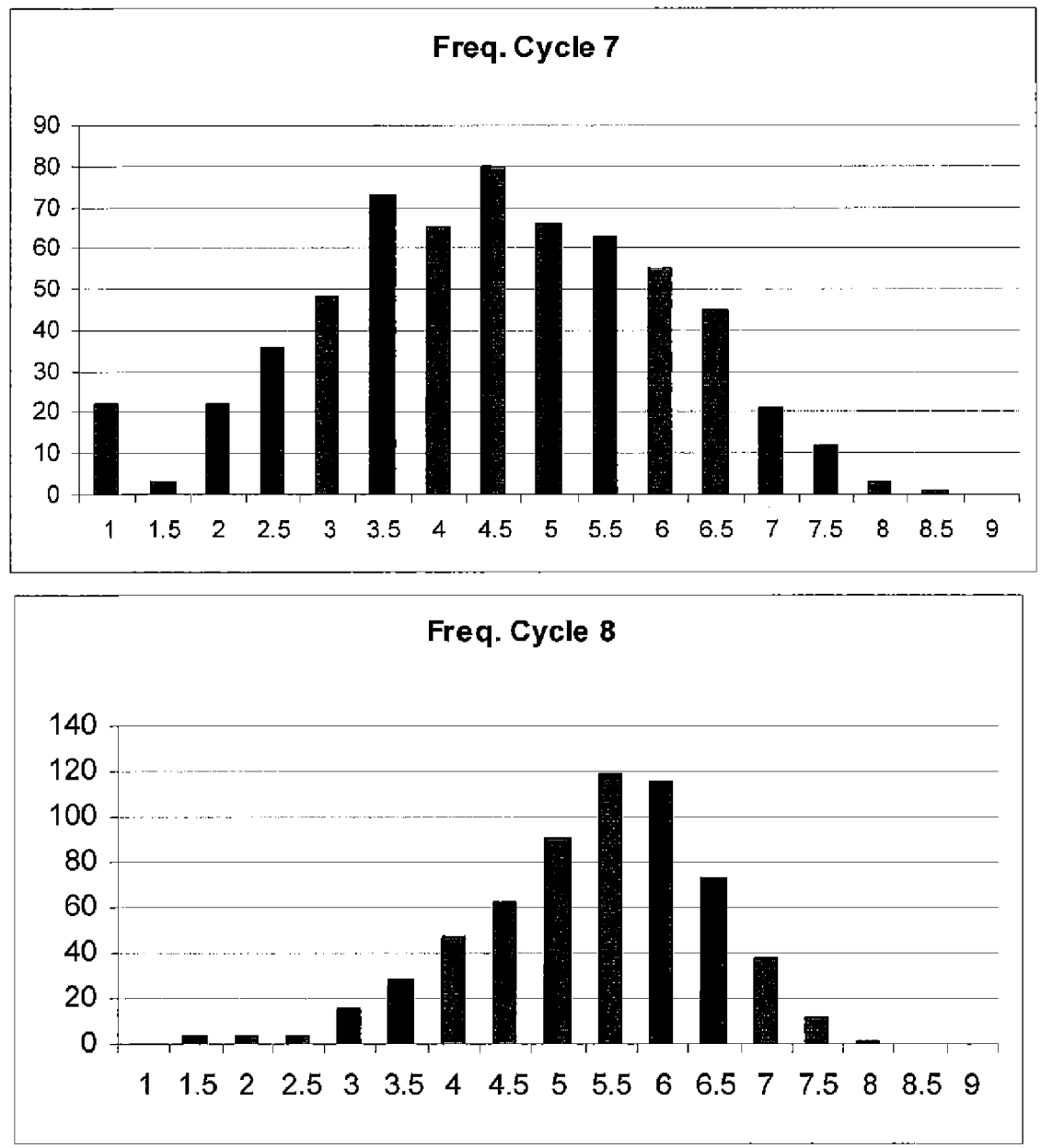
Figure 1C:
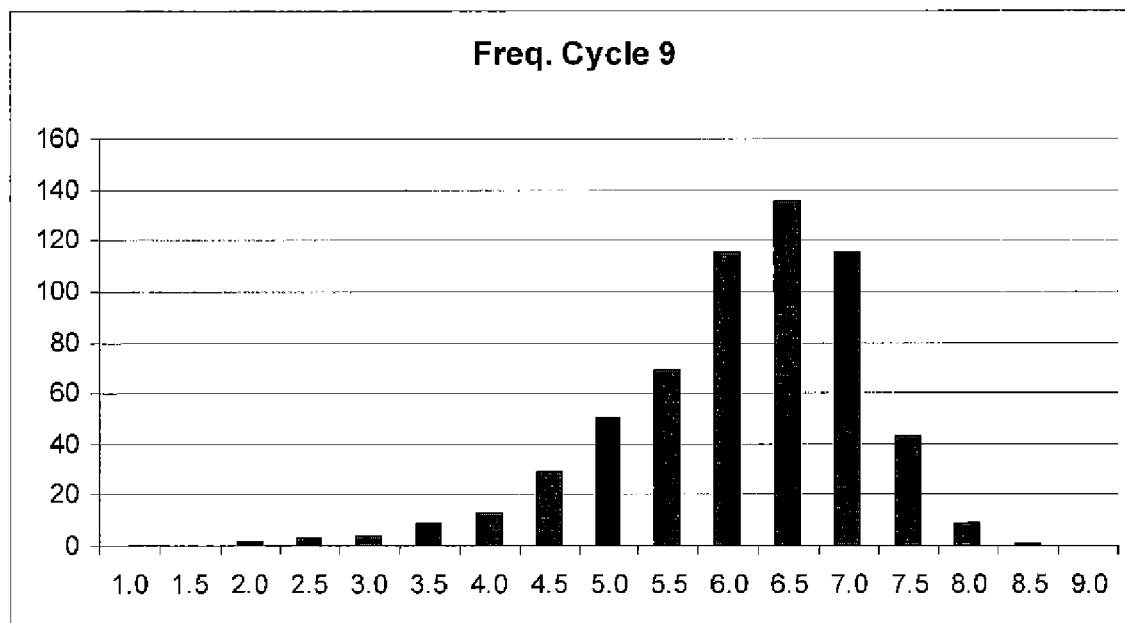
Figure 1C:
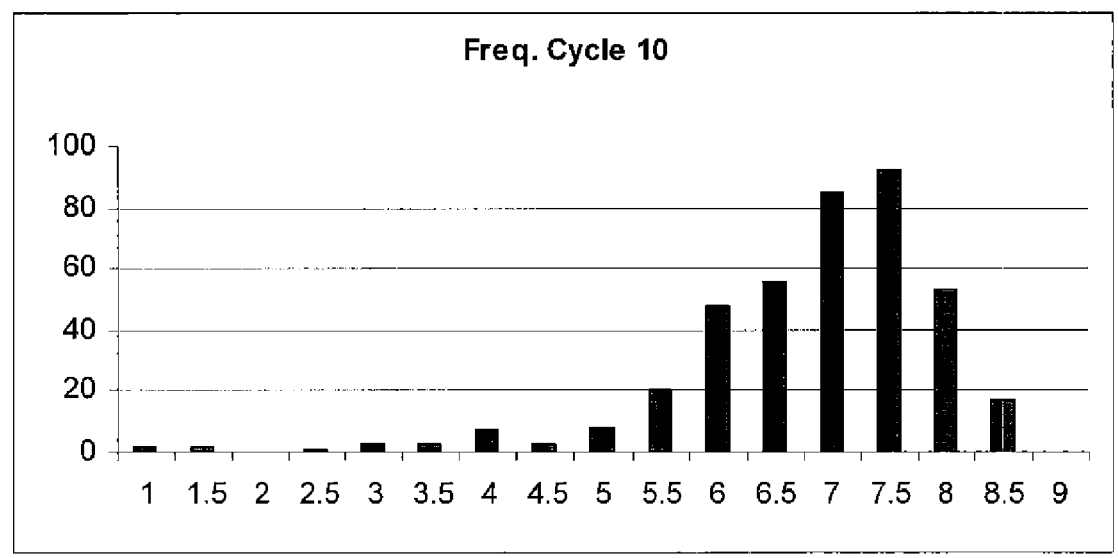

FIG. 1 is a histogram of lines generated in Cycles 5 to 10 of Population T, showing the progress toward *Sclerotinia* resistance made under extreme disease pressure field research conditions, as measured against checks in Cycles 5 to 10. With each year of Population T improvement, the percentage of disease incidence dropped and the population mean improved on the SSDI scale of 1-9. The Y-axis represents the frequency of progenies and the X-axis shows the *Sclerotinia* resistance rating on SSDI scale of 1-9 as described in Table 4. FIG. 1 shows that the mean and the mode of the population for each cycle have continually improved. For example, the mode of the population improved from 2.5 in Cycle 5, to 5.5 in Cycle 8, to 7.5 in Cycle 10. In addition, individual selections in Cycles 7, 8, and 9 had rating of 7.5, 8.0, and 8.5. Progenies exhibiting high levels of resistance were extracted and continuous improvement was observed in the field.

The extent of disease incidence in tests represented by FIG. 1 was measured under extreme disease pressure field research conditions. This is the highest possible disease pressure in natural field environments. This level of disease seldom occurs in farmers' fields (Table 3). Accordingly, it is expected that materials selected in this test will perform much better under lower and more typical disease pressure. For example, under typical moderate field disease pressure, the disease incidence for Pioneer Hi-Bred varieties 46A65 and 46A76 is generally 20-30% and 10-20% respectively (Table 3). However, under extreme disease pressure the level of disease incidence is 70% and 60% respectively (Table 3). A plant with partial field resistance exhibits (i) reduced disease development on the plant, (ii) significantly delayed onset of disease and (iii) resistance of disease development for a longer time when inoculum is in direct contact with the stem. If disease-favorable conditions persist, a significant reduction in the effect of disease is observed in partially resistant materials (Table 3 and FIG. 1).

Tables 9a, 9b and 9c describe some of the lines with improved field resistance and show their performance in the field under natural conditions in tests conducted by independent third parties. The 2004 data on SSDI % were generated in Manitoba in open-field trials under moderate disease pressure (as determined by the performance of 2 out of 3 checks). Some of the same lines were tested at the University of Minnesota (MN) under high pressure in 2003 (2 out of 2 checks) and in North Dakota (ND) under very high to extreme pressure in 2003 as per Table 3. All field resistant lines possess levels of partial stem resistance significantly higher than checks. Note that across the four locations, the performance of each of the five listed lines was well within the present claim requirements, i.e., having an average *Sclerotinia Scle-*

*rotiorum* Disease Incidence (SSDI %) score which is less than about 60% of the SSDI % score of Pioneer Hi-Bred variety 46A76 under the same environmental and disease conditions in the field.

Selections of Population T were also tested under extreme disease pressure field research conditions (Table 10a and Table 10b). Selection 02SN41269 was introduced into Cycle 8. Cycle 8 selection 03SN40441 was used to develop Cycle 9 in combination with 03SN40341 and 22 S1 lines from previous Cycle 8 as outlined in Table 8. These three lines (i.e. 02SN41269, 03SN40341 and 03SN40441) were used broadly in crossing, and Population T progenies trace back part of their genetic resistance to one or more of them.

Table 10a shows the results of three tests (two in 2004 and one in 2003) under extreme disease pressure field research conditions for 03SN40341, 03SN40441 and 02SN41269. On average, 03SN40341, 03SN40441 and 02SN41269 had a disease incidence (SSDI %) of 39%, 39% and 44% respectively, compared to 46A76. Under these extreme conditions plants are more susceptible to *Sclerotinia* for at least the reasons discussed above in the definition of "extreme disease pressure field research conditions." In contrast, a plant growing under natural field conditions (1) is not enclosed in an artificial canopy which ensures continuous moisture and (2) is grown in plots surrounded by plants with the same morphological phenotype which allows all benefits from the morphology to be expressed. Accordingly, selections having a morphology that is less conducive to *Sclerotinia* infection, for example high branching, perform significantly better under natural field conditions compared to extreme disease pressure field research conditions. For example, on average, under natural field conditions, 03SN40341, 03SN40441 and 02SN41269 had a disease incidence of 23.2%, 13.7% and 49.1% respectively, compared to 46A76, as shown in Table 9a. Accordingly, 02SN41269 has a morphology that is more conducive to *Sclerotinia* infection than 03SN40341 and 03SN40441. 02SN41269 is more prone to lodging compared to 03SN40341 and 03SN40441 (FIG. 2A). FIG. 2A reveals that 02SN41269 double haploid line 04DHS12921 as well as doubled haploid 04DHS11319 are also prone to lodging more than check 46A65 and other tested material. Low resistance to lodging can compromise *Sclerotinia* performance in natural data sets especially with a lot of moisture or excessive irrigation such as at NDSU-Carrington 2005. Research data sets bypass lodging resistance and provide scores that reflect a potential of genetic resistance in combination with morphology.

The effect of morphology under extreme disease pressure field research conditions in comparison to natural field conditions can be demonstrated using the check varieties 46A76, 46A65 and 44A89 as examples. 46A76 is one of the least susceptible varieties in the *Sclerotinia* Variety Trials in North Dakota and Minnesota University Extension trials (Tables 9a and 9b, 2003 data). 46A76 has a morphology that is less conducive to *Sclerotinia* infection compared to 46A65 or 44A89. The morphology includes features such as high branching and very good standability. Considering SSDI % scores under extreme disease pressure field research conditions (Table 10a), 44A89 is 115% of 46A76, and 46A65 is 98% of 46A76. However, in natural trials in 2004 (Table 9a), 44A89 is 232% of 46A76 and 46A65 is 199% of 46A76. This clearly shows that 46A76 is a high standard for measurement of field resistance, especially under natural field conditions, in comparison with other canola checks. This also shows the difference between natural field results and extreme disease pressure field research results. Extreme disease pressure field research conditions challenge all genotypes and represent the worst-case scenario, i.e. that which occurs normally in only 1 to 2% of natural field environments. (See, Table 3) A line which performs well under these extreme conditions is expected to perform at least as well in a natural field environment.

Inclusion of check varieties such as 44A89 and 46A76 aids in evaluation of the testing environment and of the reliability of the data generated. For example, Tables 9b and 9c compare results obtained on control lines at North Dakota and Minnesota testing sites in 2001, 2003 and 2005. These sites are extraction of higher-disease-pressure sites, excluding data sets from years with trace levels of disease (Bradley, et al., 2006). The low level of disease incidence for 46A76 in 2005 (NDSU-Carrington) indicates that environmental conditions may have complicated the disease scoring as suggested by researcher Bob Hanson (NDSU). In this instance, excessive irrigation led to both excessive lodging on earlier lines and delayed maturity on later lines, favoring later-maturing lines such as 46A76. Tables 9b and 9c suggest that the data collected at the NDSU-Carrington 2005 site are inconsistent with that generated at the same site as well as Minnesota sites in two prior years (see also, Bradley, et al., 2006).

FIG. 2 provides data on multiple trials of spring lines under both extreme disease pressure and natural field conditions. Common extreme disease pressure field research data was collected at up to four tests. Natural field data was collected at up to three locations including the North Dakota site discussed above (2005 data). When the results from the single aberrant trial are removed (FIGS. 2D and 2E), all tested lines clearly performed well within the target range, i.e. with an SSDI % score less than 60% of the SSDI % score of Pioneer variety 46A76, or of the SSDI % score of Pioneer variety 46A65, or of the mean SSDI % score of the two varieties, under the same environmental and disease conditions in the field.

Doubled haploid lines representing 02SN41269 (2 lines), 03SN40441 and 03SN40341 were extracted and characterized under extreme disease pressure field research conditions (Table 10b). The doubled haploid lines were produced by methods known to those skilled in the art; for example see Swanson, et al., (1987); Mollers, et al., (1994); Hansen, et al., (1996); U.S. Pat. No. 6,200,808; and Canadian Patent Number 2,145,833. The four doubled haploid lines had a SSDI rating of 6.6 to 7.3. This compares well against the check, Pioneer Hi-Bred variety 46A76, with a rating of 3.8. The doubled haploid lines have morphological phenotypes similar to their parental lines, and they are likely to perform better under natural conditions as well.

Table 10c provides performance data for F3 winter canola lines, 2005. The data in this Table originate from a 2005 field trial performed at Tavistock (Ontario, Canada) that was replicated three times. Extreme disease pressure was used to generate this research data set.

The field reaction of the submissions was superior to that of the checks, Express and Columbus, even under weather conditions which resulted in disease pressure higher than the target. Lodging scores on winter canola selections collected at Soest (Germany) have enabled selection of resistant material with good standability.

Table 11a shows pedigrees of five heterozygous spring canola selections (02SN41269, 03SN40341, 03SN40441, 04SN41433, and 04SN41415) and their homozygous doubled haploid progenies. Since all selections originate from a single plant (deriving 100-500 seeds for the first year of field testing) they needed to be further selfed and increased as bulks for further field testing and seed submissions.

In summary, as shown in the histogram of FIG. 1, the breeding and selection efforts over six years (2000-2005) stemming from 15 years of research (1991 to 2005) have resulted in improved spring canola lines. Under natural field conditions these lines have an average *Sclerotinia Sclerotiorum* Disease Incidence (SSDI %) score which is less than about 60% of the SSDI % score of Pioneer Hi-Bred variety 46A76, or of the SSDI % score of Pioneer Hi-Bred variety 46A65, or of the mean SSDI % score of the two varieties, under the same environmental and disease conditions in the field. Table 9a shows that Pioneer Hi-Bred variety 46A76 is one of the least susceptible canola checks in the field (rated a 3 on the SSDI scale, while most current canola products are rated 1 or 2), and represents a very challenging target against which to compare new materials. In addition, Lance™ or Endura™ are considered the most efficacious fungicides on the market. This combination of the least sensitive canola check and most efficacious fungicide sets the bar very high. As seen from the histogram of FIG. 1, Cycle 10 of Population T had an SSDI mode of 7.5, with certain individuals having a rating of 8 or 8.5. According to the rating scale in Table 4 and the results shown in FIG. 1, lines having SSDI ratings of 5, 6, 7 or 8 have been developed. They are categorized as moderately resistant (rating of 5 or 6) and resistant (rating of 7 or 8).

TABLE 9a

Summary of *Sclerotinia* natural field data results on the developed *Sclerotinia* resistant materials in 2003/2004

| VARIETY | PEDIGREE | 2004 SSDI % | 2004 SSDI % | 2003 SSDI % | 2003 SSDI % | 2003/004 SSDI % | 2003/2004 SSDI % | 2003/2004 SSFS* | 2003 SSFS | SSFS | 2003 SSFS |
|---|---|---|---|---|---|---|---|---|---|---|---|
| 2003/2004 | | MB (Morden) | MB (Carman) | ND** | MN | 4 locations | % of 46A76 | ND | MN | Mean | % of 46A76 |
| 02SN40680 | Cycle 7-BN3 | 0.6 | 1.4 | 18.5 | 4.0 | 6.1 | 23.4 | 8.4 | 0.6 | 4.5 | 20.6 |
| 02SN40209 | Cycle 7-BN4 | 4.9 | 17.4 | 22.0 | 0.0 | 11.1 | 42.3 | 10.1 | 0 | 5.1 | 23.1 |
| 02SN41269 | 02SN40102-BN1 | 4.0 | 1.4 | 39.0 | 7.0 | 12.9 | 49.1 | 16.6 | 3.5 | 10.1 | 46.0 |
| 46A76 | MS check | 18.3 | 14.6 | 51.0 | 21.0 | 26.2 | 100.0 | 25.6 | 18.1 | 21.9 | 100.0 |
| 44A89 | HS check | 42.2 | 35.4 | 90.0 | 76.0 | 60.9 | 232.4 | 64.8 | 76.0 | 70.4 | 322.2 |
| 2004 only | | | | | | 2 locations | % of 46A76 | | | | |
| 03SN40441 | Cycle 8 | 1.7 | 2.8 | | | 2.2 | 13.7 | | | | |
| 03SN40341 | Cycle 8 | 3.2 | 4.4 | | | 3.8 | 23.2 | | | | |
| 46A65 | S check | 33.3 | 32.0 | | | 32.6 | 198.8 | | | | |

*Field severity at ND and MN is calculated by multiplying disease incidence (SSDI %) with disease severity on infected plants and dividing by 5 (SSFS = [SSDI % × SSDS(0-5 scale)] ÷ 5). A lower severity '1' versus dead plant '5' will significantly decrease overall impact of the disease as seen by comparing 44A89 vs. 02SN40680.
ND = North Dakota
MN = Minnesota
MB = Manitoba TABLE 9b NDSU and University of Minnesota natural data on canola variety field reaction to *Sclerotinia* (% disease incidence) 2001/2003/2005*

| Cultivar | 2001 Carrington | 2001 Red Lake Falls | 2003 Carrington[1] | 2003 Red Lake Falls[2] | 2005 Carrington | 2001-2003 Mean | ALL Mean |
|---|---|---|---|---|---|---|---|
| Hylite201** | 14.7 | 15 | 65.0 | 4.0 | 41 | 25 | 28 |
| Hyola401 | 20.7 | 33 | 55.0 | 11.0 | 54.5 | 30 | 35 |
| 46A76 | 22.7 | 34.7 | 51.0 | 21.0 | 16.0 | 32 | 29 |
| Hyola357 | 34.0 | 41 | 60.5 | 18.0 | 55.5 | 38 | 42 |
| LG3455 | 41.3 | 41 | 52.5 | 29.0 | 30 | 41 | 39 |
| 44A89 | 36.0 | 73 | 90.0 | 76.0 | 49.5 | 69 | 65 |

*Data generated by Bob Hanson (NDSU) and Dave Legare (University of Minnesota)
**Apetalous canola
[1]Carrington (North Dakota) 2003 data corresponds to Table 9a 2003 ND data
[2]Red Lake Falls (Minnesota) 2003 data corresponds to Table 9a 2003 MN data TABLE 9c NDSU (Carrington) and University of Minnesota (Red Lake Falls) natural data on canola variety field reaction to *Sclerotinia* (disease incidence) 2001/2003*, expressed as % of 46A76

| Cultivar | 2001 Carrington *Sclerotinia* incidence (%) | 2001 Red Lake Falls | 2003 Carrington | 2003 Red Lake Falls | 2005 Carrington | 2001-2003 Mean | ALL Mean |
|---|---|---|---|---|---|---|---|
| Hylite201** | 65 | 42 | 127 | 19 | 256 | 63 | 102 |
| Hyola401 | 91 | 96 | 108 | 52 | 341 | 87 | 138 |
| 46A76 | 100 | 100 | 100 | 100 | 100 | 100 | 100 |
| Hyola357 | 150 | 118 | 119 | 86 | 347 | 118 | 164 |

TABLE 9c-continued

NDSU (Carrington) and University of Minnesota (Red Lake Falls) natural data on canola variety field reaction to *Sclerotinia* (disease incidence) 2001/2003*, expressed as % of 46A76

| Cultivar | 2001 Carrington *Sclerotinia* incidence (%) | 2001 Red Lake Falls | 2003 Carrington | 2003 Red Lake Falls | 2005 Carrington | 2001-2003 Mean | ALL Mean |
|---|---|---|---|---|---|---|---|
| LG3455 | 182 | 119 | 103 | 138 | 188 | 135 | 146 |
| 44A89 | 159 | 211 | 176 | 362 | 309 | 227 | 243 |

*Data generated by Bob Hanson (NDSU) and Dave Legare (University of Minnesota)
**Apetalous canola

TABLE 10a

Summary of extreme disease pressure research data 2003-2004 sources (SSDI) 3 tests

| Variety | 2004 TEST 1 SSDI | Flower** | 2004 TEST 2 SSDI | Flower | 2003 TEST 3 SSDI | Flower | Mean SSDI | Mean Flower | Conversion* | SSDI % of 46A76 |
|---|---|---|---|---|---|---|---|---|---|---|
| 03SN40341 | 5.8 | 48 | 7.2 | 48 | 7.2 | 44 | 6.7 | 46.7 | 23 | 39 |
| 03SN40441 | 5.6 | 46 | 6.8 | 49 | 7.8 | 45 | 6.7 | 46.7 | 23 | 39 |
| 02SN41269 | 5.9 | 44 | 6.6 | 45 | 6.6 | 41 | 6.4 | 43.3 | 26 | 44 |
| 46A76 | 3.8 | 48 | 2.0 | 52 | 3.4 | 44 | 3.1 | 48.0 | 59 | 100 |
| 46A65 | 2.9 | 46 | 3.2 | 46 | 3.6 | 42 | 3.2 | 44.7 | 58 | 98 |
| 44A89 | n/a | n/a | 2.5 | 47 | 1.8 | 46 | 2.2 | 46.5 | 68 | 115 |

*Table 4 conversion 1-9 for SSDI into SSDI %
**50% of flower

TABLE 10b

Extreme disease pressure field research data on doubled haploid lines and their parental sources (02SN41269, 03SN40441 and 03SN40341) selected for a high level of field resistance.

| SSDI | FLOWER | VARIETY | PEDIGREE |
|---|---|---|---|
| 6.8 | 48 | 04DHS11319 | POPTC8-03SN40041 Doubled haploid |
| 6.6 | 48 | 04DHS11418 | POPTC8-03SN40050 Doubled haploid |
| 7.0 | 47 | 04DHS12921 | 03SN40919 Doubled haploid |
| 7.3 | 47 | 04DHS12927 | 03SN40919 Doubled haploid |
| 5.8 | 48 | 03SN40341 | POPTC8-03SN40041 Cycle 8 |
| 5.6 | 46 | 03SN40441 | POPTC8-03SN40050 Cycle 8 |
| 5.9 | 44 | 02SN41269 | 02SN40102 |
| 1.9 | 49 | NS3181BR | Susceptible Roundup DH |
| 3.8 | 48 | 46A76 | Moderately susceptible check |
| 2.9 | 46 | 46A65 | Susceptible check |

TABLE 10c

Performance of F3 winter canola lines against *Sclerotinia* (Tavistock, Ontario) and their agronomic/quality traits (Soest, Germany) 2005.

| VARIETY-F3 | PEDIGREE | SSDIS | Conversion | % mean of combined checks | Lodging* | Height* | Erucic acid 22:1 | **Glucosinolates | VARIETY-F2 |
|---|---|---|---|---|---|---|---|---|---|
| 04CWB930128 | 03CWB925237-10 | 6.3 | 27 | 42 | 6.0 | 7 | 0.03 | 19.1 | 03CWB925237 |
| 04CWB930127 | 03CWB925237-7 | 6.3 | 27 | 42 | 6.0 | 7.0 | 0.16 | 7.9 | 03CWB925237 |
| 04CWB930081 | 03CWB925200-4 | 5.9 | 31 | 48 | 6.0 | 4.0 | 0.03 | 8.1 | 03CWB925200 |
| 04CWB930111 | 03CWB925024-9 | 5.8 | 32 | 49 | 6.0 | 5 | 0.02 | 9.9 | 03CWB925024 |
| 04CWB930144 | 03CWB925261-5 | 5.4 | 36 | 55 | 6.0 | 3.0 | 0.10 | 8.3 | 03CWB925261 |
| 04CWB930015 | 03CWB925059-1 | 5.3 | 37 | 57 | 8.0 | 5.0 | 0.02 | 18.5 | 03CWB925059 |
| 04CWB930135 | 03CWB925245-3 | 5.3 | 37 | 57 | 6.0 | 8.0 | 0.20 | 17.2 | 03CWB925245 |
| Columbus | Columbus | 2.0 | 70 | 108 | | | | | Columbus |
| Express | Express | 3.0 | 60 | 92 | 6.2 | 5.1 | 0.02 | 15.0 | Express |

*Lodging (1 lodged - 9 erect) and Height (1 short - 9 tall) scores from Soest, Germany, 2005
**Glucosinolate content determined on F3 samples from Soest, Germany, 2005

TABLE 11a

Pedigrees of three spring canola selections and their doubled haploid progenies

| Line # | Pedigree | Status | *Field testing samples |
|---|---|---|---|
| 41269 and DHS | | | |
| 04DHS12921 | 03SN40919 | Doubled haploid deposited as ATCC Accession No: PTA-6781 | |
| 04DHS12927 | 03SN40919 | Doubled haploid | |
| 03SN40919 | 02SN40102 | F5 bulk increase 02SN41269 | |
| 03SN40918 | 02SN40102 | F4 bulk increase out of 02SN41269 Deposited as 02SN41269 ATCC Accession No: PTA-6777 | 2003 onward |
| 02SN41269 | 02SN40102 | F3 from a single F2 plant | 2002 |
| 02SN40102 | 01SN41722 | F2 568 F3s selected for field test | |
| 01SN41722 | 01SN41702 × 01SN41209 | F1 | |
| 01SN41702 | 01SN41338 × 01SN41277 | F1 | |
| 01SN41338 | POPTC5 × (PGR8493 × (POPTC3 × NS1602)) | F3 selection out of 60 field-tested | |
| 01SN41277 | POPTC5 × (PGR8492 × (POPTC3 × NS2082)) | F3 selection out of 33 field-tested | |
| 01SN41209 | POPTC5 × (PGR8488 × (POPTC3 × NS1602)) | F3 selection out of 73 field-tested | |
| 40341 and DHS | | | |
| 04DHS11319 | POPTC8-03SN40041 | Doubled haploid deposited as ATCC Accession No: PTA-6780 | |
| 04SN441521 | POPTC8-03SN40041 | 04SN441521-S3 bulk increase out of 04SN40006 deposited as 03SN40341 ATCC Accession No: PTA-6776 | 2004 onward |
| 04SN40006 | POPTC8-03SN40041 | S2 bulk GH increase out of 03SN40341 | |
| 03SN40341 | POPTC8-03SN40041 | 03SN40341-S1 out from single S0 plant | 2003 |
| 40441 and DHS | | | |
| 04DHS11418 | POPTC8-03SN40050 | Doubled haploid deposited as ATCC Accession No: PTA-6778 | |
| 04SN441522 | POPTC8-03SN40050 | 04SN441522-S3 bulk increase out of 04SN40009 deposited as 03SN40441 ATCC Accession No: PTA-6779 | 2004 onward |
| 04SN40009 | POPTC8-03SN40050 | S2 bulk GH increase out of 03SN40441 | |
| 03SN40441 | POPTC8-03SN40050 | 03SN40441-S1 from single S0 plant | 2003 |
| 41433 and DHS | | | |
| 05DHS12897 | POPTC9-04SN40049 | Doubled haploid; NCIMB Accession No: 41391 | |
| 05SN-41433 | POPTC9-04SN40049 | S2 bulk increase, deposited as 04SN-41433 NCIMB Accession No: 41389 | 2005 onward |
| 04SN-41433 | POPTC9-04SN40049 | S1 out of single S0 plant Cycle 9 | 2004 |
| 41415 and DHS | | | |
| 04DHS12879 | POPTC9-04SN40047 | Doubled haploid; NCIMB Accession No.: 41390 | |
| 05SN-41415 | POPTC9-04SN40047 | S2 bulk increase, deposited as 04SN-41415 NCIMB Accession No: 41388 | 2005 onward |
| 04SN-41415 | POPTC9-04SN40047 | S1 out of single S0 plant Cycle 9 | 2004 |

*segregating material originated from a single S1 or F3 plant and was increased for subsequent years of testing after the first year TABLE 11b Pedigrees of 7 winter canola submissions

| NCIMB Deposit | F4** Deposits | F3* From a single F2 plant | F2** Selected F2 with a designated single plant out of it |
|---|---|---|---|
| 41395 | 05CWB940127 | 04CWB930127 | 03CWB925237-7 |
| 41396 | 05CWB940128 | 04CWB930128 | 03CWB925237-10 |
| 41393 | 05CWB940081 | 04CWB930081 | 03CWB925200-4 |
| 41394 | 05CWB940111 | 04CWB930111 | 03CWB925024-9 |
| 41398 | 05CWB940144 | 04CWB930144 | 03CWB925261-5 |
| 41397 | 05CWB940135 | 04CWB930135 | 03CWB925245-3 |
| 41392 | 05CWB940015 | 04CWB930015 | 03CWB925059-1 |

*F1 progeny of the complex cross {[CV0242 × 01CWB940022] × [(00FWB940100 × 00FWB940919) × 01CWB910012]} were selfed and selected in the greenhouse for Sclerotinia reaction.
** Selection for Sclerotinia reaction and quality was made among 400 F2 lines in an unreplicated field screen.
*** Selection for Sclerotinia reaction, lodging, and quality was made among 200 F3 lines in a field test with three replications. Each F3 line is descended from a single F2 plant.
*** F4 bulk increase in plots, Soest 2005 harvest for a patent deposit as the increase of the F3 selected generation from a single plant TABLE 11c Components of complex cross for *Sclerotinia* resistance in winter canola.

| Component | | Parentage*** | Resistance Components | Generation | Comments |
|---|---|---|---|---|---|
| 1 | 01CWB940022 | 97CWN39131 × (CV0058 × CV0057) | PI469955 | F4 | Indoor screen (4 out of 16 plants selected) before further crossing |
| | 01CWB930022 | 97CWN39131 × (CV0058 × CV0057) | PI469955 | F3 | Indoor screen (4 out of 16 plants selected) |
| | 01CWB920022 | 97CWN39131 × (CV0058 × CV0057) | PI469955 | F2 | Indoor screen (4 out of 16 plants selected) |
| | 01CWB910022 | (97CWN39131 × (CV0058 × CV0057) | PI469955 | F1 | Cross |
| | 97CWN39131 | CV0065 × PI469955 | PI469955 | F3 | selection for canola quality (erucic acid) and resistance 4 plants per selection (glucosinolates on seeds)-testing 20 low erucic F2 families |
| | 96CWN29131 | CV0065 × PI469955 | PI469955 | F2 | self to produce 1,300 seeds for erucic acid cotyledon test |
| | 95CWN19131 | CV0065 × PI469955 | PI469955 | F1 | cross |
| 2* | 99FWB940100 | (CV0043 × CV0063) × 97CWN39191 | PI469830 | F4 | |
| | 97CWN39191 | CV0114 × PI469830 | PI469830 | F3 | |
| 3* | 00FWB940919 | ((CV0063 × CV0059) × (CV0060 × CV0011)) × 97CWN39260 | PI470079 | F4 | |
| | 97CWN39260 | CV0087 × PI470079 | PI470079 | F3 | |
| 4* | 01CWB910012 | NW3978 × (CV0060 × 00SN42757) | PopT Cycle 6 | BC1F1 | |
| Table 8 description | 00SN42757 | PopT Cycle 6 (Table 8) | PopT Cycle 6 (Table 8) | F2 | bulk pollen from Cycle 6 Pop T 3,000 plants |

**Component 2 and 3 generated in the same way as Component 1
***CV and NW codes refer to *Sclerotinia*0-susceptible elite varieties from Pioneer's winter canola collection

Example 3

Canola Determination

According to the Canola Council of Canada, canola is defined by the following properties: The oil must contain less than 2% erucic acid and the solid component of the seed must contain less than 30 micromoles of any one or any mixture of 3-butenyl glucosinolate, 4-pentenyl glucosinolate, 2-hydroxy-3 butenyl glucosinolate and 2-hydroxy-4-pentenyl glucosinolate per gram of air-dry, oil free solid.

The erucic acid level and glucosinolates content were measured to verify that the seed produced by Population T conforms to the definition of canola. The erucic acid level was measured by whole seed fatty acid profile and the glucosinolate level was measured by scanning NIR as described below:

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of J. K. Daun, et al., (1983) which is herein incorporated by reference.

Glucosinolate Content. The total glucosinolates of seed at 8.5% moisture as measured by AOCS Official Method AK-1-92 (Determination of glucosinolates content in rapeseed —colza by HPLC) is expressed micromoles per gram. Capillary gas chromatography of the trimethylsityl derivatives of extracted and purified desulfoglucosinolates with optimization to obtain optimum indole glucosinolate detection is described in "*Procedures of the Western Canada Canola/Rapeseed Recommending Committee Incorporated for the Evaluation and Recommendation for Registration of Canola/Rapeseed Candidate Cultivars in Western Canada.*"

Canola must also meet the requirements of the growing season agronomically. For spring canola, the average number of days to reach 50% flowering typically falls within the range of 30-90 days (Table 1). In order to control for the growth conditions in any one year or in any one field, the number of days to flowering is compared with official check varieties growing in the same field and under the same conditions. Table 12 summarizes the results of the glucosinolate, erucic acid, days to 50% flowering and days to maturity tests in comparison to the official WCC/RRC (*Western Canada Canola/Rapeseed Recommending Committee Incorporated for the Evaluation and Recommendation for Registration of Canola/Rapeseed Candidate Cultivars in Western Canada*) check varieties, 46A65 and Q2. As can be seen in Table 12, the plants produced by Population T are comparable to the checks and meet the definition for spring canola. Variation within an acceptable range may occur due to environmental differences.

TABLE 12

Canola quality/spring habit - erucic acid (C22:1)/glucosinolates/flowering/maturity

| Variety | C22:1* | | Glucosinolates** | | Flower 50% | Maturity | Source |
|---|---|---|---|---|---|---|---|
| Ontario 2004 | | | | | | | |
| 02SN40209 | 0.06 | low | 11.98 | low | 48.3 | 102.5 | Pop T |
| 02SN40680 | 0.06 | low | 27.79 | low | 48.2 | 102.5 | Pop T |

TABLE 12-continued

Canola quality/spring habit - erucic acid (C22:1)/glucosinolates/flowering/maturity

| | | | | | | | |
|---|---|---|---|---|---|---|---|
| 02SN41269 | 0.00 | low | 14.50 | low | 44.7 | 100.8 | related to Pop T |
| 03SN40341 | 0.08 | low | 11.53 | low | 47.8 | 102.7 | Pop T |
| 03SN40441 | 0.13 | low | 11.42 | low | 46.2 | 101.3 | Pop T |
| 03SN40698 | 0.10 | low | 13.59 | low | 45.0 | 103.2 | Pop T |
| 46A76 | 0.13 | low | 11.15 | low | 50.2 | 102.8 | Check |
| 46A65*** | 0.11 | low | 16.24 | low | 47.0 | 102.0 | Official Check |
| Q2*** | 0.07 | low | 13.02 | low | 50.0 | 102.0 | Official Check |

Chile 04/05
Variety    C:22:1

| | | | | | | | |
|---|---|---|---|---|---|---|---|
| 04DHS11319 | 0.01 | low | 15.97 | low | 59.0 | 119 | 03SN40341 |
| 04DHS11418 | 0.01 | low | 12.56 | low | 63.5 | 118.5 | 03SN40441 |
| 04DHS12921 | 0.01 | low | 20.12 | low | 57.0 | 114 | 02SN41269 |
| 04DHS12927 | 0.02 | low | 20.65 | low | 57.0 | 116 | 02SN41269 |
| 04SN41415 | 0.02 | low | 10.39 | low | 60 | 113 | Pop T |
| 04SN41433 | 0.02 | low | 10.38 | low | 63 | 116 | Pop T |
| 46A65 | 0.01 | low | 14.65 | low | 59.0 | 114 | Official check |

Chile 05/06
Variety

| | | | | | | | |
|---|---|---|---|---|---|---|---|
| 05DHS12879 | 0.02 | low | 9.91 | low | 62 | 114 | 04SN41415 |
| 05DHS12897 | 0.02 | low | 9.98 | low | 65 | 114 | 04SN41433 |
| 46A65 | 0.03 | low | 14.31 | low | 67 | 118 | Official check |

*percentage of total fatty acids - Erucic (C22:1)
**glucosinolates (u mole - total aliphatic glucs/g airdryed meal)
***official registration quality checks

Example 4

Trait Complexity

Table 13 shows the complexity of the genetic segregation in crosses with susceptible elite material aimed at product development. While the efficacy data in FIG. 1 shows trait performance, the segregation data in Table 13 shows low recovery of partially resistant lines. This indicates that the pyramided genetic components result in complex segregation. It is estimated that three or four genes are conferring partial resistance in these materials. Introgression of these three or four genes into elite material requires significant effort. The greater the contribution of susceptible elite material, the more difficult the introgression of the *Sclerotinia* resistance genes. For example, it will be easier to introgress the *Sclerotinia* resistance genes into material that contains 50% susceptible elite material compared to material that contains 75% susceptible elite material. Haploid techniques can be used to fix the segregating progeny in a similar fashion as was used to fix the sources of resistance shown in Tables 10a, 10b and 10c.

TABLE 13

Outcome of breeding activities - recovery of resistant progenies after crossing partially resistant selections with susceptible elite lines in 2003 and 2004*

| Field Year | Gen | % Susceptible parent Contribution | # of plants started in GH test | GH selections in Field test | Final # of field selected lines | Success of breeding % GH-started | Success of breeding % Field-started |
|---|---|---|---|---|---|---|---|
| 2003 | BC1F$_3$ | 75 | 1870 | 170 | 3 | 0.2 | 1.8 |
| 2003 | F$_2$ | 50 | 500 | 260 | 6 | 1.3 | 2.3 |
| 2004 | BC1F$_3$ | 75 | 2400 | 455 | 46 | 2 | 11 |
| 2004 | F$_2$ | 50 | 122 | 122 | 20 | 15 | 15** |
| 2004 | BC1F$_3$ | 25 | 630 | 235 | 39 | 6 | 16 |

*Different sources used in different years/projects
**Lateness inflated the number of selections significantly. The lines flowered later compared to checks

Example 5

Screening for Blackleg Resistance

Blackleg (*Leptosphaeria maculans* and other *Leptosphaeria* species), also known as phoma stem canker, is an internationally important disease of *Brassica*, causing significant economic losses in Europe, Australia, and North America. (Fitt, et al., 2006) Progenies of Population T were screened for blackleg resistance by the methods outlined in procedures of WCC/RRC, in "*Procedures of the Western Canada Canola/Rapeseed Recommending Committee Incorporated for the Evaluation and Recommendation for Registration of Canola/Rapeseed Candidate Cultivars in Western Canada*", herein incorporated by reference.

Table 14 describes blackleg ratings from two locations in Western Canada with the most virulent races of the disease. The selections 02SN41269 and 02SN40441 were found to have high levels of adult plant resistance to blackleg with a 2004 mean rating of 8.7 compared to the susceptible check, Westar, which had a rating of 5.8. (Table 14) Data collected in 2005 also indicated that blackleg resistance of 02SN41269 and 03SN40441 is superior to 46A76.

Field observations in Tavistock (2004 and 2005) indicate that resistance of winter lines to blackleg is similar to that of Columbus/Express.

TABLE 14

Reaction of experimental materials to blackleg in Western Canada, 2004/2005

| Variety | Blackleg reaction | Plum Coulee, Manitoba | Killam, Alberta | 2004 Mean* | Killam, Alberta 2005 |
|---|---|---|---|---|---|
| 02SN41269 | | 8.9 | 8.5 | 8.7 | 6.3 |
| 03SN40441 | | 8.5 | 8.8 | 8.7 | 5.5 |
| 46A65 | Resistant Check | 7.0 | 8.4 | 7.7 | 4.6 |
| Q2 | Resistant Check | 7.1 | 8.0 | 7.6 | N/A |
| 03SN40341 | | 7.0 | 7.5 | 7.3 | 4.7 |
| 03SN40698 | | 6.0 | 8.4 | 7.2 | 5.2 |
| 02SN40209 | | 6.3 | 7.8 | 7.0 | N/A |
| 02SN40680 | | 6.3 | 7.3 | 6.8 | 5.2 |
| 46A76 | | 4.9 | 8.5 | 6.7 | 3.6 |
| 04DHS11319 | | | | | 3.8 |
| 04DHS12921 | | | | | 5.6 |
| 04DHS11418 | | | | | 6.5 |
| 04SN-41415 | | | | | 5.8 |
| 04SN-41433 | | | | | 5.3 |
| WESTAR | Susceptible check | 6.4 | 5.2 | 5.8 | 3.3 |

*1 = dead plant, 9 = no symptoms of disease

Example 6

Greenhouse and Growth Chamber Screening for *Sclerotinia* Resistance

Development of methodologies to screen for *Sclerotinia* in the greenhouse/growth rooms was one of the critical success factors in developing *Sclerotinia* resistant *Brassica* lines. It is well established that generating reliable data for *Sclerotinia* screening is problematic.

The following method was developed to evaluate canola stem and/or leaf reaction to *Sclerotinia* stem rot in the greenhouse and growth room. This method was used to develop and screen the *Sclerotinia* resistant lines of Examples 1, 2, 3, 4 and 5. Although the methods described are directed to *Brassica*, it is to be understood that any plant susceptible to *Sclerotinia* can be used, for example soybean or sunflower.

Uniformity

*Sclerotinia* interacts with both the environment and the plant, and disease development reflects all aspects of that interaction. In order to obtain the most accurate results in breeding for *Sclerotinia* resistance, the maximum uniformity of (1) plant materials (growth stage, stem or leaf size, inoculation point), (2) inoculum, and (3) the environment (humidity chambers, growth rooms or compartments) must be attained. This is a requirement for collection of reliable data.

*Sclerotinia* and Media

PDA (potato dextrose agar) can be used for propagating *Sclerotinia*. The medium is rich in nutrients, allowing rapid fungal growth. Also, plant tissue can be infected via PDA. Thus, PDA is very good for the initial transfer, and for situations where higher or faster infection pressure needs to be exerted, for example in very late growth stages or when a short turnaround time is required for the material.

For more sensitive tests, PDA low-nutrient should be used. Mycelial growth and the infection process are slowed, and the plant material stands a better chance of expressing its typical reaction. Also, the infection process can be more reliably interrupted so selections have a better chance of producing seeds. The steps listed below may be followed:

| Media | |
|---|---|
| PDA—Potato Dextrose Agar | |
| Media Ingredients | 1 L |
| PDA (Potato Dextrose Agar) | 39 g. |
| PDA low nutrient | |
| Media Ingredients | 1 L |
| PDB (Potato Dextrose Broth) | 12 g |
| Agar (Sigma A-1296) | 15 g |

1. Retrieve sclerotia of *S. sclerotiorum* isolate.
2. Cut sclerotia in half aseptically and place cut side down on a plate of PDA.
3. Incubate in the dark at 19° C. (+/−3° C.) for 72 to 90 hours or until the mycelium nearly reaches the edge of the plate. One can use lower temperatures to slow down the growth (4-16° C.).
4. For inoculation in the greenhouse or growth room cut plugs of approximately 2-4 mm in diameter using a cork borer. It is preferred to use plugs from the outside ring of mycelium, where mycelium is uniformly developed, so all plugs are of a similar age and quality.

Stem Inoculation Method

One can inoculate canola after stem elongation until physiological maturity, i.e. seed color change. In the field, the plant is affected during the petal drop stage. Generally, early-infected plants are more susceptible and accordingly older plants are less susceptible. Depending on the objective of the screening, one can inoculate from pre-flowering to post-flowering. Plants can be grown in 32-cell flats or 4-inch (and bigger) pots. Bigger and more robust plants are more resistant to *Sclerotinia*. Smaller and thinner plants are more susceptible. It is not recommended to test internodes, but points close to the nodes just above the leaf axils, to simulate natural infection. *Sclerotinia* susceptible and/or partially resistant checks should be included in the screening.

Entomological Needle Method

For plants tested in a humidity chamber, a needle inoculation, for example an entomological needle, method can be used. A 3 mm plug (+/−1 mm) is prepared and probed with a needle, for example stainless entomological needle #1 to #3. The needle is used to support the attachment of the plug supporting the mycelium to the stem. The method enables one to test a large number of plants. The plants may be thin, for example when grown in 32-cell flats. The steps listed below may be followed:

1. Inoculation can be performed at a single or multiple points on the stem depending on the purpose of the experiment.
2. Place the plants in the humidity chamber or humid environment for approximately 20 to 60 hours or until symptoms start developing. Observe the reaction of the susceptible and/or partially resistant checks. Remove inoculum (limited term inoculation) and cease the incubation in humidity when the fresh lesion length on most of the plants of a susceptible and/or partially resistant check is at least 5-30 mm, depending on the objective of screening. Lesion length is the most reliable parameter. Initial selections can be made immediately after incubation in the chamber, as initial reaction is a good indication of performance.
3. Move plants to the greenhouse/growth room bench and record the lesion length and growth stage after incubation where needed. Ensure that plants are not allowed to dry out. Growth stage can be recorded prior to inoculation if needed.
4. Selection should be performed relative to the desired target and checks or relative to performance of adjacent plants.
5. If needed for experimental purposes, measure lesion length and the rate of disease severity (1-9) when satisfactory differentiation is attained or after one and two weeks. This can vary relative to the progress of disease development on plants. While rating disease severity, take into account lesion length, stem stiffness and extent of girdling.
6. Avoid conducting inoculation experiments during summer months when greenhouse temperatures are elevated. If needed, experiments can be conducted in the growth room, preferably with an increase in air humidity.

Use of the entomological needles and small-diameter low-nutrient PDA plugs with mycelium has enabled the screening of a large number of plants and has enabled multiple inoculations on a single plant in order to verify the reaction. This is very important in selecting and advancing the most resistant progenies to the field for further evaluation.

Sclerotinia rating scale (SSDS indoor—Sclerotinia sclerotiorum disease severity indoor)
1—Prematurely ripened or dead plant
3—Large lesion, weak and completely-girdled stem
5—Large lesion >30 mm, stiff and nearly-girdled stem
7—Small lesion <30 mm, stiff and not-girdled stem
9—No lesion Intermediate scores can be assigned if symptom severity falls in between defined scores.

A less humid and a well aerated environment can be used after infection to help infected flowering plants survive infection.

Leaf Inoculation Method

Leaf inoculation is performed in order to detect differences in the level of resistance of different entries. It is performed at earlier growth stages than stem inoculation, e.g. pre-bolting, for an early detection of partial resistance. However, leaf screening is normally conducted at flowering, and can occur in the field within whole plant evaluation. As leaves are more sensitive to Sclerotinia compared to stem, low-nutrient PDA should be used unless otherwise specified. Intact leaves can be inoculated with plugs, or plugs with entomological needles, for testing and selection purposes. The steps listed below may be followed:

1. Large-scale screening can be conducted in a humidity chamber. It is important that the level of moisture in the chamber is sufficiently high to enable infection to occur, yet not excessive as free water impedes fungal infection.
2. Take 2-4 mm plug preferably from the outer 1 cm of colony edge with uniform mycelial cover and place the plug upside down on the leaf. Position the plug to leave as much leaf area as possible for lesion development.
3. Do not attempt to measure lesion diameter unless there is uniform development of lesions around the plugs. Avoid having plugs without good leaf contact. If these occur, count them as escapes. Measure leaf lesion diameter in millimeters before the fungus has reached the end of the available leaf tissue on susceptible check or when deemed appropriate.
4. Remove the material from the humidity chamber after uniform lesion establishment around plugs (or good differentiation between susceptible and resistant checks) and keep material under the regular humidity conditions. Visual selection relative to the checks or the adjacent plants is done for both parameters, against sensitive reaction(s) or combinations of moderate and sensitive reactions.

Example 7

Field Screening for Sclerotinia Resistance Under Extreme Disease Pressure Field Research Conditions Methodology improvements were critical to success in developing Sclerotinia-resistant Brassica lines. It is well established that generating reliable field data on an annual basis is not common. Sclerotinia is a potent disease but it only develops during wet summers with moderate temperatures. A number of issues become critical in screening for Sclerotinia resistance in the field in years when the conditions of Sclerotinia are sub-optimal. Duration of wetness, water quality, availability of inoculum, and presence of moist or humid microenvironments affect disease development in the crop. Although the methods described are directed to Brassica, it is to be understood that the methods may be applied to any plant susceptible to Sclerotinia infection via ascospores. This includes sunflower (head rot), safflower (head rot), dry bean (pod rot), dry pea (pod rot), soybean (stem and pod rot), alfalfa (blossom blight), and lettuce (lettuce drop). Bardin and Huang, 2001. See also, US Patent Application Publication Number 2003/0150016 for Sclerotinia effects in soybean.

The critical issues in the field have been resolved as follows:
(a) Appropriate artificial inoculum for continuum of data collection: Since natural inoculum is not always triggered in the field, an inoculum that mimics infection via petals has been developed. The carrier for the fungus can be Niger seed (Guizotia abyssinica-Nyer seed) colonized with Sclerotinia and distributed at the time of full petal drop.
(b) Water quality and Sclerotinia: Initially, ground water was used to irrigate the Sclerotinia colonized fields. However, a lack of infection transfer in years with low rainfall and either high or low temperatures was observed. In vitro tests have confirmed that ground water inhibits Sclerotinia growth. Through lab and field testing, it was determined that deionizing (DI) water treatment alters the ground water quality sufficiently to prevent inhibition of Sclerotinia development. Henceforth, DI water was used to irrigate extreme disease pressure field research plots. In theory, the treated deionized water differs from the original ground water in that the minerals, for example magnesium and calcium (lime), are eliminated while the pH is not affected. *Sclerotinia* produces oxalic acid, a diffusible toxin, to aid in the infection process (U.S. Pat. No. 6,380, 461). Calcium can bind with oxalic acid to create calcium oxalate. Removal of calcium is very likely the qualitative change in the deionized water that enables growth of *Sclerotinia*. Accordingly, a water source low in minerals or having no minerals, for example reduced or eliminated magnesium and calcium, can be used.

(c) Irrigation operated by leaf-wetness sensors: To enable continuous wetness in the field, leaf wetness sensors (Campbell Scientific) that trigger irrigation only if moisture is lower than a set threshold are used. Optimized irrigation enables disease development and enhances screening for disease resistance. However, excess irrigation may interfere with meaningful evaluation. In particular, in a research setting with rows of unique genotypes in close proximity, lodging of one entry can lead to transfer of the pathogen by plant-to-plant contact and increased disease incidence on a second genotype. Thus the *Sclerotinia* resistance score for the second genotype may underestimate its potential performance in a more homogeneous population. In natural field data trials, excessive irrigation can create a more conducive environment for *Sclerotinia* through an increase in lodging over what is usual for a given genotype. Thus, the performance of the trial entries may be distorted due to excessive irrigation, such as occurred in the 2005 NDSU test. (See, FIG. 2)

(d) Providing an enclosure to help maintain a microenvironment necessary for disease development: To enable development of disease in dry, hot and/or windy seasons, a netting enclosure may be used.

These new methodologies coupled with the breeding and crossing efforts described above enabled the careful selection of *Sclerotinia*-resistant canola lines. The new methodologies enable controlled disease development, reliable expression of phenotype, and characterization of many different lines under optimal *Sclerotinia* conditions in order to make the progress shown in the histogram of FIG. 1.

The following method was developed to screen for *Sclerotinia* resistance in the field.

Uniformity

*Sclerotinia* interacts with the environment and plant material. The data gathered reflect_all aspects of this interaction. In order to reduce variability, a maximum uniformity of (1) plant material, (2) inoculum and (3) environment is required. This is a prerequisite for collection of viable data.

Site Selection/Experimental Design/Planting

1. Identify the site that may be colonized with sclerotia for a natural back-up inoculum together with artificial inoculum. If the site is not colonized with sclerotia one can attempt to produce sclerotia via infection of alternative hosts such as soybeans or white beans, inoculate using a carrier such as Niger seed, or introduce sclerotia directly.
2. Plant entries in replicated plots or rows if possible. Use Randomized Complete Block Design (RCBD) with appropriate susceptible and/or resistant checks (RCBD has each unit of experimental material present in each of the blocks (replications)). Attempt to keep experiments small to decrease the error due to environmental variation. Running checks should be used and performance expressed relative to the checks. Maturity of the checks should correspond to maturity of the lines being tested.
3. Attempt to grow a dense and healthy canola crop to promote disease development. Seed rates should be uniform. Precision planting is preferred, or plants can be thinned to a uniform number of plants. To promote disease development, consider using a windbreak by planting strips or additional passes and/or installing netting around or over the crop.

Favorable Environment/Irrigation/Back-Up Natural Infection

Development of *Sclerotinia* stem rot is environmentally-dependent and the presence of inoculum is not sufficient unless a favorable wet or humid microenvironment is established within the crop. The relative success of infection is measured by the degree to which the susceptible checks are affected within the experiment.

As natural infection is seldom reliable or uniform, irrigation systems are used to promote disease development. Irrigation may be initiated as soon as the crop produces an enclosed canopy so that the canopy can retain moisture. Before the onset of flowering, the goal is to keep the topsoil wet and condition the sclerotia for germination to enable the development of apothecia in order to produce ascospores for the colonization of the petals.

Once the petals are colonized, the goal is to enable the progression of the disease to the leaves and stems after sufficient petal drop. This transfer occurs naturally in years with prolonged wet or humid conditions. Leaf wetness sensors regulate moisture in the canopy by triggering irrigation when the canopy is dry. The transfer of disease can be inhibited with ground water (especially in lower temperatures) so, if feasible, use collected rainwater or deionized ground water. Moisture in the canopy is needed until stem infection on the susceptible checks is fully developed.

While the environment is important for disease development, attained disease incidence and severity are directly related to the timing of the following factors: favorable environment, growth stage and inoculum pressure.

A netting enclosure can be used to preserve wet or humid conditions and enable disease development.

Inoculum Preparation/Artificial Infection

Artificial inoculum is used as a primary inoculum to increase disease pressure at the site and enable development of disease similar to the extreme disease pressure. Natural inoculum is a back-up inoculum in this case. Niger seeds colonized with *Sclerotinia* may be used as a carrier for this purpose. The steps listed below may be followed:

1. Prepare PDA plates of *Sclerotinia*, incubate at 19° C. (+/−3° C.) for 3-6 days or until the colonies nearly reach the edge of plate as described in Example 6.
2. Place five to six mycelial plugs (2-4 mm diameter) into flasks with 200 ml (+/−100 ml) PDB with 0.5 g/l streptomycin to initiate production of fresh mycelium.
3. Incubate in the dark at 19° C. (+/−3° C.) for 2-3 days on the shaker at 1.2 rpm.
4. Extract PDB from hyphal mass, homogenize hyphal mass in the blender, add Tween™ (approximately 0.5 ml/l) and dilute to 1-3 g (optimum 2 g) of fresh mycelium/1 L of water for field inoculation. PDB may be added back once the mycelium is weighed out. For colonizing Niger seed with inoculum use the following procedure: Autoclave the seed twice using ratio 1:2 of $H_2O$:Niger. After the Niger has cooled, add about 100 ml PDB: 500 g Niger and incubate at room temperature in the dark. One can use straight PDB or dilute it as needed. Once incubation and the development of the fungal inoculum on the seed is complete, dry the inoculum and break the clumps of seeds. This typically takes between 5 and 15 days. To simulate and enhance natural infection, the inoculum can be applied during significant petal drop.
5. Ensure that sufficient Niger inoculum is available before flowering.

6. *Sclerotinia*-colonized Niger seeds are sieved prior to application. Colonized seeds can be spread over plant material by hand. For large-scale inoculation, a fertilizer spreader or other spreading device, for example a mistblower, can be used to distribute the Niger seeds. The application should be carried out in the front and the back of each range.
7. Approximately 5-20 kg/ha of Niger seed are used. The uniformity and quality of the distribution should be verified.
8. The goal of the Niger application is to produce a number of leaf lesions per plant that may progress to stem infection.
9. The *Sclerotinia*-colonized Niger seed application should be repeated if needed.

Rating

The percentage of infected plants and disease severity can be rated (Tables 2 and 15) once the targeted incidence and extent of stem symptoms have developed on susceptible and/or resistant checks. It is recommended to conduct one rating when the desired differentiation is attained. Subsequent ratings are less reliable as the results may be affected by the physical impact on the canopy and stand during the initial rating. The rating is adjusted relative to the effect that the symptoms may have on the yield of the affected plant. For example, girdling on the lower stem versus on the higher stem has more effect on yield. Affected side racemes will reduce yield in pods that are only on that raceme, while an affected main raceme will affect the pods on the whole plant. This is reflected in the SSDS score; see, Table 15.

Number and position of rated plants per row or plot are to be determined relative to the plant and disease development within the experiment. Disease pressure tends to be most uniform in the middle of rows or plots. Atypical and small plants should be excluded from the count and preferably pulled out of the row prior to or at counting. Thinning early in the season would resolve this issue. If possible, outside plants should not be rated.

In order to enable viable comparison of material and account for environmental variation, trials contain running checks such as 46A65 and 46A76.

TABLE 15

Guidelines for scoring severity of symptoms on a single-plant basis in the field - Pioneer SSDS field - *Sclerotinia sclerotiorum* disease severity - field. Numbers in brackets designate public scale.

| Pioneer SSDS Scale of 1 to 9 Public scale 0-5 in brackets( ) | Symptoms<br>Main Stem | <br>Primary Branches (Off main stem) | <br>Secondary Branches (Off primary) | <br>Pods | Approximate Yield loss (%) |
|---|---|---|---|---|---|
| 1 (5) | Prematurely Ripened Plant - dead | | | | 50 |
| 2 (5) | Girdled and weak - will affect yield | | | | 40-50 |
| 3 (4) | Girdled but less yield reducing | Most dead or dying branches | | | 30-40 |
| 4 (3) | At least 50% girdled; Some yield impact | Many dead or dying branches | | | 20-30 |
| 5 (2) | Very Large lesion | Few dead or dying branches | | | 10-20 |
| 6 (2) | Large lesion | One dead or dying branch | Multiple dead or dying branches | Multiple Infected Pods | 5-10 |
| 7 (1) | Medium Lesion (~30 mm) | Girdled branch | Few dead or dying Branches | Few infected pods | 1-5 |
| 8 (1) | Small Lesion | Branch with non-girdling lesion | One dead or dying branch | One infected pod | 1 |
| 9 (0) | No Symptoms | No symptoms | No Symptoms | No symptoms | 0 |

The methods of Examples 6 and 7 required significant technical human intervention and were used in the development of the *Sclerotinia*-resistant lines of the present invention. Significant human technical intervention allowed year-round testing of selections and provided consistent and reproducible results. In addition, the method of example 7 allowed the development of extreme disease conditions every year, regardless of the natural environment.

Example 8

Producing Inbred Lines Having Resistance to *Sclerotinia*

Table 13 outlines efforts in inbred line development and success in developing elite inbreds in 2003 and 2004. The trait is complex, comprising approximately 3-4 genes in materials from elite crosses tested in 2003/2004. Since the material in Population T is canola quality (Table 12), different approaches as outlined in Table 13 are available. Trait recovery (i.e. *Sclerotinia* resistance) is feasible in straight crosses where elite inbreds provide 50% of the genetics ($F_2$).

BC1 into resistant sources enables easier recovery of the trait but the compromise is a lower proportion of the genetic background of the elite inbreds. It is possible to fully recover resistance by breeding BC2 or higher with resistant backgrounds if the primary goal is to recover resistance, with lower consideration for other breeding issues, for example quality, hybrid vigour, etc. BC1 into susceptible elites is aimed at recovery of elite backgrounds (75%) and the *Sclerotinia* resistant trait, but recovery of the *Sclerotinia* resistant trait becomes more challenging.

Once elite lines with field resistance are recovered, new breeding approaches are possible where recovery of resistance becomes more feasible (field resistant elite crossed by field resistant elite, for example). Recovering resistance in such crosses is relatively easy and the F1 material can be subjected to doubled haploidy and resistant progenies genetically stabilized, i.e. fixed, for a repeatable and predictable response.

Example 9

Producing Hybrids Having Resistance to *Sclerotinia*

Due to the fact that partial resistance is not dominant, it is necessary to have resistance in both the male and female inbreds involved in hybrid seed production. Thus, field resistant inbreds must be developed in female as well in male pools of genetic materials. Hybrid crops are known for higher yields compared to their inbred components due to heterosis based on the genetic distance between female and male components of a hybrid.

By crossing well-established susceptible female and male inbreds (Table 13) with the *Sclerotinia*-resistant lines of the present invention, elite lines with field resistance are recovered having various combinations of elite background and resistant background (for example 25-75% of elite background as shown in Table 13). Such newly developed female and male inbreds have both field resistance as well as the genetic distance previously established in their elite but susceptible parental lines. Similar to regular hybrid breeding, extensive field testing is subsequently used to determine which inbred combinations provide high yield as well as an adequate level of field resistance to *Sclerotinia*.

Once a number of elite female and male lines capable of producing hybrids with high yield and field resistance to *Sclerotinia* are identified, further progress can be made by crossing such lines and developing inbreds that will further elevate yield as well as field resistance to *Sclerotinia*.

Accordingly, the invention includes not only those lines particularly described herein, but any descendent or progeny, in particular progeny produced by extracting doubled haploid lines, having the *Sclerotinia* resistance trait. The invention also includes any hybrids produced using the lines described herein. Further, the invention includes seeds, plant cells and cellular materials, including pollen and ovules, derived from the improved plants, lines, or progeny. Plant cells can be isolated from plants as is known to those skilled in the art. For example, see, Chuong, et al., (1985); Barsby, et al., (Spring 1996); Kartha, et al., (1974); Narasimhulu, et al., (Spring 1988); and Swanson, (1990).

Plants from the present invention can be used to grow a crop as is known to those skilled in the art. Further, plants from the present invention can be used for oil and meal production. Seeds from plants of the present invention can be used to produce canola oil as is known to those skilled in the art. The method may include crushing the seeds, extracting crude oil from the seeds, and refining, bleaching and deodorizing the crude oil to produce the canola oil. Canola meal can be produced as is known to those skilled in the art. Accordingly, the invention also includes crushed seeds from the plants of the present invention.

Finally, the plants of the present invention can be used for breeding as is known to those skilled in the art, particular examples of which are described below.

V. Further Embodiments Of The Invention

The inbred and hybrid lines of examples 8 and 9 can be achieved using methods of plant breeding as are known to those skilled in the art, as described above, and as described below. In addition to inbred and hybrid line development, the invention is also directed to methods for using the *Sclerotinia* resistant lines of this invention to meet other plant breeding objectives.

One such embodiment is the method of crossing the *Sclerotinia* resistant lines of this invention with another canola plant to form a first generation population of F1 plants. The population of first generation F1 plants produced by this method is also an embodiment of the invention. This first generation population of F1 plants will comprise an essentially complete set of the alleles of the *Sclerotinia* resistant lines of this invention. Typically in the art an F1 hybrid is considered to have all the alleles of each homozygous parent. One of ordinary skill in the art can utilize either breeder books or molecular methods to identify a particular F1 plant produced using the *Sclerotinia* resistant lines of this invention, and any such individual plant is also encompassed by this invention. These embodiments also cover use of these methods with transgenic or single gene conversions of the *Sclerotinia* resistant lines of this invention.

Another embodiment of this invention is a method of using the *Sclerotinia* resistant lines of this invention in breeding that involves the repeated backcrossing to the *Sclerotinia* resistant lines of this invention any number of times. Using backcrossing methods, or the transgenic methods described herein, the single gene conversion methods described herein, or other breeding methods known to one of ordinary skill in the art, one can develop individual plants and populations of plants that retain at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% of the genetic profile of the *Sclerotinia* resistant lines of this invention. The percentage of the genetics retained in the progeny may be measured by either pedigree analysis or through the use of genetic techniques such as molecular markers or electrophoresis. In pedigree analysis, on average 50% of the starting germplasm would be passed to the progeny line after one cross to another line, 25% after another cross to a different line, and so on. Molecular markers could also be used to confirm and/or determine the pedigree of the progeny line.

A specific method for producing a line derived from the *Sclerotinia* resistant lines of this invention is as follows. One of ordinary skill in the art would cross a *Sclerotinia* resistant line of this invention with another canola plant, such as an elite line. The F1 seed derived from this cross would contain a single copy of 100% of the alleles from the *Sclerotinia* resistant line of this invention and a single copy of 100% of the alleles of the other plant. The F1 seed would be grown to form a homogeneous population and allowed to self, thereby forming F2 seed. On average the F2 seed would have derived 50% of its alleles from the *Sclerotinia* resistant line of this invention and 50% from the other canola plant, but various individual plants from the population would have a much greater percentage of their alleles derived from the *Sclerotinia* resistant lines of this invention (Wang and Bernardo, 2000 and Bernardo and Kahler, 2001). The F2 seed would be grown and selection of plants would be made based on visual observation and/or measurement of traits. The traits used for selection may be the traits associated with the *Sclerotinia* resistant lines of this invention. The derived progeny that exhibit the desired traits of the *Sclerotinia* resistant lines of this invention would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants. The process of growing and selection would be repeated any number of times until an inbred of the *Sclerotinia* resistant line of this invention is obtained. The inbred of the *Sclerotinia* resistant line of this invention would contain the *Sclerotinia* resistant trait.

If the other canola plant to which the *Sclerotinia* resistant line was crossed also contained *Sclerotinia* resistance genes, then an inbred developed from the progeny may exhibit *Sclerotinia* resistance at a level equal to or greater than the level expressed in the *Sclerotinia* resistant line of this invention. An inbred would have, on average, 50% of its genes derived from the *Sclerotinia* resistant lines of this invention, but various individual plants from the population would have a much greater percentage of their alleles derived from the *Sclerotinia* resistant line of this invention. The breeding process of crossing, selfing, and selection may be repeated to produce another population of the *Sclerotinia* resistant lines of the invention-derived canola plants with, on average, 25% of their genes derived from the *Sclerotinia* resistant line of this invention, but various individual plants from the population would have a much greater percentage of their alleles derived from the *Sclerotinia* resistant line of this invention.

The previous example can be modified in numerous ways; for instance, selection may or may not occur at every selfing generation, selection may occur before or after the actual self-pollination process occurs, or individual selections may be made by harvesting individual pods, plants, rows, or plots at any point during the breeding process described. In addition, doubled haploid breeding methods may be used at any step in the process. The population of plants produced at each and any generation of selfing is also an embodiment of the invention.

Another embodiment of this invention is the method of obtaining homozygous *Sclerotinia* resistant lines by crossing a *Sclerotinia* resistant line of this invention with another canola plant and applying doubled haploid methods to the F1 seed or F1 plant or to any generation of the *Sclerotinia* resistant lines of this invention obtained by the selfing of this cross.

Still further, this invention also is directed to methods for producing the *Sclerotinia* resistant lines of this invention by crossing a *Sclerotinia* resistant line of this invention with a canola plant and growing the progeny seed, and repeating the crossing and the growing steps with the *Sclerotinia* resistant line of this invention from 1 to 2 times, 1 to 3 times, 1 to 4 times, or 1 to 5 times and selfing any number of times after the first, second, third, fourth, or fifth cross.

Thus, any and all methods using one or more of the *Sclerotinia* resistant lines of this invention in breeding are part of this invention, including selfing, pedigree breeding, backcrosses, hybrid production and crosses to populations. All plants and populations of plants produced using one or more of the *Sclerotinia* resistant lines of this invention as a parent are within the scope of this invention. Unique molecular marker profiles and/or breeding records can be used by those of ordinary skill in the art to identify the progeny lines or populations of progeny derived from one or more of the *Sclerotinia* resistant lines of this invention.

All plants produced using a *Sclerotinia* resistant line of this invention as a parent are within the scope of this invention, including those developed from progeny derived from the inbred of a *Sclerotinia* resistant line of this invention.

A further embodiment of the invention is a single gene conversion of the *Sclerotinia* resistant lines of this invention. A single gene conversion occurs when DNA sequences are introduced through traditional (non-transformation) breeding techniques, such as backcrossing. DNA sequences, whether naturally-occurring or transgenes, may be introduced using these traditional breeding techniques. Desired traits transferred through this process include, but are not limited to, fertility modification, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single gene traits may result from the transfer of either a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive allele. Recessive traits may require additional progeny testing in successive backcross generations to determine the presence of the gene of interest. Along with selection for the trait of interest, progeny are selected for the phenotype of the recurrent parent. It should be understood that occasionally additional polynucleotide sequences or genes are transferred along with the single gene conversion trait of interest. Progeny containing at least 90%, 95%, 96%, 97%, 98%, 99% or 99.5% of the genes from the recurrent parent, the canola plant disclosed herein, plus containing the single gene conversion trait, is considered to be a single gene conversion of the *Sclerotinia* resistant lines of this invention.

It should be understood that the *Sclerotinia* resistant lines of the invention can, through routine manipulation of cytoplasmic genes, nuclear genes, or other factors, be produced in a male-sterile form as described in the references discussed earlier. Such embodiments are also within the scope of the present claims. The *Sclerotinia* resistant lines of this invention can be manipulated to be male sterile by any of a number of methods known in the art, including by the use of mechanical methods, chemical methods, self-incompatibility, cytoplasmic male sterility (either ogura or another system) or nuclear male sterility. The term "manipulated to be male sterile" refers to the use of any available techniques to produce a male sterile version of a *Sclerotinia* resistant line of this invention. The male sterility may be either partial or complete male sterility. This invention is also directed to F1 hybrid seed and plants produced by the use of the *Sclerotinia* resistant lines of this invention.

This invention is also directed to the use of the *Sclerotinia* resistant lines of this invention in tissue culture. As used herein, the term plant cell includes plant protoplasts, plant cell tissue cultures from which canola plants can be regenerated, plant calli, plant clumps, and plant cells that are intact in plants or parts of plants, such as embryos, pollen, ovules, seeds, flowers, ears, silique, leaves, stems, roots, root tips, anthers, cotyledons and the like. Tissue culture as well as microspore culture for regeneration of canola plants can be accomplished successfully. (Chuong, et al., (1985); Barsby, et al., (Spring 1996); Kartha, et al., (1974); Narasimhulu, et al., (Spring 1988); Swanson, (1990). Thus, it is clear from the literature that the state of the art is such that these methods of obtaining plants are, and were, "conventional" in the sense that they are routinely used and have a very high rate of success.

The utility of the *Sclerotinia* resistant lines of this invention also extends to crosses with other species. Commonly, suitable species will be of the family *Brassica*. In particular, *Sclerotinia*-resistant winter lines may be sources of resistance in breeding programs for spring or semi-winter lines. *Sclerotinia*-resistant spring lines may be sources of resistance in breeding programs for semi-winter or winter lines. All such uses are contemplated by, and made a part of, the present invention.

The advent of new molecular biological techniques have allowed the isolation and characterization of genetic elements with specific functions, such as encoding specific protein products. Scientists in the field of plant biology have developed a strong interest in engineering the genome of plants to contain and express foreign genetic elements, or additional or modified versions of native or endogenous genetic elements, in order to alter the traits of a plant in a specific manner. Any DNA sequences, whether from a different species or from the same species that are inserted into the genome of the species using transformation are referred to herein collectively as "transgenes". The process of "transforming" is the insertion of DNA into the genome. Over the last fifteen to twenty years, several methods for producing transgenic plants have been developed, and the present invention, in particular embodiments, also relates to transformed versions of the claimed *Sclerotinia* resistant lines of this invention.

Numerous methods for plant transformation have been developed, including biological and physical plant transformation protocols. See, for example, Miki, et al., (1988). In addition, expression vectors and in vitro culture methods for plant cell or tissue transformation and regeneration of plants are available. See, for example, Evans, et al., (1983), Binding (1985) and Weissbach, et al., 1988.

The most prevalent types of plant transformation involve the construction of an expression vector. Such a vector comprises a DNA sequence that contains a gene under the control of, or operatively linked to, a regulatory element, for example a promoter. The vector may contain one or more genes and one or more regulatory elements.

A genetic trait which has been engineered into a particular canola plant using transformation techniques could be moved into another line using traditional breeding techniques that are well known in the plant breeding arts. For example, a backcrossing approach could be used to move a transgene from a transformed canola plant to an elite inbred line and the resulting progeny would comprise a transgene. Also, if an inbred line was used for the transformation then the transgenic plants could be crossed to a different line in order to produce a transgenic hybrid canola plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. See, U.S. Pat. No. 6,222,101 which is herein incorporated by reference.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr (1981).

A genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule coding for the foreign protein. For exemplary methodologies in this regard, see, Glick and Thompson, (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons could involve hybridizations, RFLP, PCR, SSR and sequencing, all of which are conventional techniques.

Likewise, by means of the present invention, plants can be genetically engineered to express various phenotypes of agronomic interest. Exemplary transgenes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1993); Mindrinos, et al.

(B) A protein conferring resistance to fungal pathogens, such as oxalate oxidase or oxalate decarboxylase (Zhou, et al., (1998), U.S. Pat. Nos. 3,303,846 and 6,297,425).

(C) A *Bacillus thuringiensis* protein, a derivative thereof or a synthetic polypeptide modeled thereon. See, for example, Geiser, et al., (1986), who disclose the cloning and nucleotide sequence of a Bt δ-endotoxin gene. Moreover, DNA molecules encoding δ-endotoxin genes can be purchased from American Type Culture Collection (Manassas, Va.), for example, under ATCC Accession Numbers 40098, 67136, 31995 and 31998.

(D) A lectin. See, for example, the disclosure by Van Damme, et al., (1994), who disclose the nucleotide sequences of several *Clivia miniata* mannose-binding lectin genes.

(E) A vitamin-binding protein such as avidin. See, PCT Application Number US93/06487, the contents of which are hereby incorporated by reference. The application teaches the use of avidin and avidin homologues as larvicides against insect pests.

(F) An enzyme inhibitor, for example, a protease or proteinase inhibitor or an amylase inhibitor. See, for example, Abe, et al., (1987) (nucleotide sequence of rice cysteine proteinase inhibitor), Huub, et al., (1993) (nucleotide sequence of cDNA encoding tobacco proteinase inhibitor I), Sumitani, et al., (1993) (nucleotide sequence of *Streptomyces nitrosporeus* α-amylase inhibitor) and U.S. Pat. No. 5,494,813 (Hepher and Atkinson, issued Feb. 27, 1996).

(G) An insect-specific hormone or pheromone such as an ecdysteroid and juvenile hormone, a variant thereof, a mimetic based thereon, or an antagonist or agonist thereof. See, for example, the disclosure by Hammock, et al., (1990), of baculovirus expression of cloned juvenile hormone esterase, an inactivation of juvenile hormone.

(H) An insect-specific peptide or neuropeptide which, upon expression, disrupts the physiology of the affected pest. For example, see the disclosures of Regan, (1994) (expression cloning yields DNA coding for insect diuretic hormone receptor), and Pratt, et al., (1989) (an allostatin is identified in *Diploptera puntata*). See also, U.S. Pat. No. 5,266,317 to Tomalski, et al., who disclose genes encoding insect-specific, paralytic neurotoxins.

(I) An insect-specific venom produced in nature by a snake, a wasp, etc. For example, see Pang, et al., (1992), for disclosure of heterologous expression in plants of a gene coding for a scorpion insectotoxic peptide.

(J) An enzyme responsible for a hyperaccumulation of a monterpene, a sesquiterpene, a steroid, hydroxamic acid, a phenylpropanoid derivative or another non-protein molecule with insecticidal activity.

(K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993), who teach the nucleotide sequence of a cDNA encoding tobacco hookworm chitinase, and Kawalleck, et al., (1993), who provide the nucleotide sequence of the parsley ubi4-2 polyubiquitin gene.

(L) A molecule that stimulates signal transduction. For example, see the disclosure by Botella, et al., (1994), of nucleotide sequences for mung bean calmodulin cDNA clones, and Griess, et al., (1994), who provide the nucleotide sequence of a maize calmodulin cDNA clone.

(M) A hydrophobic moment peptide. See PCT Application Number WO95/16776 (disclosure of peptide derivatives of Tachyplesin which inhibit fungal plant pathogens) and PCT Application Number WO95/18855 (teaches synthetic antimicrobial peptides that confer disease resistance), the respective contents of which are hereby incorporated by reference.

(N) A membrane permease, a channel former or a channel blocker. For example, see the disclosure by Jaynes, et al., (1993), of heterologous expression of a cecropin-β lytic peptide analog to render transgenic tobacco plants resistant to *Pseudomonas solanacearum*.

(O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

(P) An insect-specific antibody or an immunotoxin derived therefrom. Thus, an antibody targeted to a critical metabolic function in the insect gut would inactivate an affected enzyme, killing the insect. Cf. Taylor, et al., (1994) (enzymatic inactivation in transgenic tobacco via production of single-chain antibody fragments).

(Q) A virus-specific antibody. See, for example, Tavladoraki, et al., (1993), who show that transgenic plants expressing recombinant antibody genes are protected from virus attack.

(R) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See, Lamb, et al., (1992). The cloning and characterization of a gene which encodes a bean endopolygalacturonase-inhibiting protein is described by Toubart, et al., (1992).

(S) A developmental-arrestive protein produced in nature by a plant. For example, Logemann, et al., (1992), have shown that transgenic plants expressing the barley ribosome-inactivating gene have an increased resistance to fungal disease.

(T) Gene products involved in the Systemic Acquired Resistance (SAR) Response and/or the pathogenesis related gene products. Briggs, (1995).

(U) Antifungal gene products (Cornelissen and Melchers, (1993) and Parijs, et al., (1991) and Bushnell, et al., (1998)).

2. Genes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988), and Miki, et al., (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European Application Number 0 242 246 to Leemans, et al., (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop, are the Acc1-S1, Acc1-S2 and Acc1-S3 genes described by Marshall, et al., (1992).

(C) A herbicide that inhibits photosynthesis, such as a triazine (psbA and gs+ genes) and a benzonitrile (nitrilase gene). Przibilla, et al., (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441 and 67442. Cloning and expression of DNA coding for a glutathione S-transferase is described by Hayes, et al., (1992).

3. Genes that Confer or Contribute to a Value-Added Trait, Such as:

(A) Modified fatty acid metabolism, for example, by transforming a plant with an antisense gene of stearoyl-ACP desaturase to increase stearic acid content of the plant. See, Knultzon, et al., (1992).

(B) Decreased phytate content
  (1) Introduction of a phytase-encoding gene would enhance breakdown of phytate, adding more free phosphate to the transformed plant. For example, see, Van Hartingsveldt, (1993), for a disclosure of the nucleotide sequence of an *Aspergillus niger* phytase gene.
  (2) A gene could be introduced that reduces phytate content. In maize, this could be accomplished, for example, by cloning and then reintroducing DNA associated with the single allele which is responsible for maize mutants characterized by low levels of phytic acid. See, Raboy, et al., (1990).

(C) Modified carbohydrate composition effected, for example, by transforming plants with a gene coding for an enzyme that alters the branching pattern of starch. See, Shiroza, et al., (1988) (nucleotide sequence of *Streptococcus mutans* fructosyltransferase gene), Steinmetz, et al., (1985) (nucleotide sequence of *Bacillus subtilis* levansucrase gene), Pen, et al., (1992) (production of transgenic plants that express *Bacillus licheniformis* α-amylase), Elliot, et al., (1993) (nucleotide sequences of tomato invertase genes), Sogaard, et al., (1993) (site-directed mutagenesis of barley α-amylase gene), and Fisher, et al., (1993) (maize endosperm starch branching enzyme II).

(D) Reduced green seed, by down regulation of the CAB gene in Canola seed (Morisette et al., 1997)

(E) Elevated oleic acid via FAD-2 gene modification and/or decreased linolenic acid via FAD-3 gene modification (see, U.S. Pat. Nos. 6,063,947; 6,323,392; and WO 93/11245).

4. Genes that Control Pollination or Hybrid Seed Production; for Example, Canadian Patent Number 2,087,703.

INDUSTRIAL APPLICABILITY

The seed of the *Sclerotinia* resistant lines of this invention, the plant produced from such seed, the hybrid canola plant produced from the crossing of the *Sclerotinia* resistant lines of this invention, the resulting hybrid seed, and various parts of the hybrid canola plant can be utilized in the production of an edible vegetable oil or other food products in accordance with known techniques. For example, a method of producing canola oil may comprise: (a) crushing canola seed; (b) extracting crude oil; and (c) refining, bleaching and deodorizing the crude oil to produce canola oil. The remaining solid meal component derived from seeds can be used as a nutritious livestock feed.

VI. Deposits

Certain deposits of seed have been made with the American Type Culture Collection (ATCC), Manassas, Va. 20852, which is the deposits include 2500 seeds of each of 02SN41269 (F4), PTA-6777; 04DHS12921 (doubled haploid), PTA-6781; 03SN40341 (F4), PTA-6776; 04DHS11319 (doubled haploid), PTA-6780; 03SN40441 (F4), PTA-6779; 04DHS11418 (doubled haploid), PTA-6778. The seeds deposited with ATCC were and have been maintained by Pioneer Hi-Bred International, Inc., 800 Capital Square, 400 Locust Street, Des Moines, Iowa 50309-2340, since prior to the filing date of this application. The deposits will be maintained in the ATCC depository, which is a public depository, for a period of 30 years, or 5 years after the most recent request, or for the effective life of the patent, whichever is longer, and will be replaced if they become nonviable during that period. Additionally, Applicant has satisfied all the requirements of 37 C.F.R. Sections 1.801-1.809. Applicant imposes no restrictions on the availability of the deposited material from the ATCC; however, Applicant has no authority to waive any restrictions imposed by law on the transfer of biological material or its transportation in commerce. Applicant does not waive any infringement of his rights granted under this patent. Access to these deposits will be available during the pendency of the application to the Commissioner of Patents and Trademarks and to persons determined by the Commissioner to be entitled thereto upon request. Applicant does not waive any infringement of his rights granted in any under this patent and/or under the Plant Variety Protection Act (7 USC 2321 et seq.).

Additional deposits of seed were made in May 2006 with NCIMB Ltd., of Aberdeen, Scotland, a public depository recognized by the Budapest Treaty, as follows:
NCIMB 41388 *Brassica napus* 04SN 41415
NCIMB 41389 *Brassica napus* 04SN 41433
NCIMB 41390 *Brassica napus* 05DHS 12879
NCIMB 41391 *Brassica napus* 05DHS 12897
Deposit date 12 May 2006.
NCIMB 41392 *Brassica napus* 04CWB 930015
NCIMB 41393 *Brassica napus* 04CWB 930081
NCIMB 41394 *Brassica napus* 04CWB 930111
NCIMB 41395 *Brassica napus* 04CWB 930127
NCIMB 41396 *Brassica napus* 04CWB 930128
NCIMB 41397 *Brassica napus* 04CWB 930135
NCIMB 41398 *Brassica napus* 04CWB 930144
Deposit date 15 May 2006

Details regarding these deposited lines are shown in Tables 11a and 11b. In each case, 3000 seed were deposited, except for NCIMB 41393, for which only 400 seeds were deposited due to limited supply. A supplemental deposit can be made, if needed.

Additionally, a deposit of isolate SS#4 of *Sclerotinia sclerotiorum* was made to the International Depositary Authority of Canada, Winnipeg, Manitoba on May 17, 2006, and assigned accession number 170506-01. This isolate was used for all indoor screening and selection methods, and extreme disease pressure field research conditions, described herein. Natural field research data, such as is set forth in Tables 9a, 9b and 9c, reflects testing against the natural population of *Sclerotinia* and confirms the efficacy of breeding efforts using the SS#4 isolate.

The foregoing invention has been described in detail by way of illustration and example for purposes of exemplification. However, it will be apparent that changes and modifications such as single gene modifications and mutations, seasonal variants, variant individuals selected from populations of the plants of the lines described, and the like, are considered to be within the scope of the present invention. All references disclosed herein, whether to journal, patents, published applications or the like, are hereby incorporated in their entirety by reference.

It should be understood that certain modifications should be and will be apparent to those of ordinary skill in the art, and that such modifications to the precise lines, varieties, and procedures described in the invention are intended to come within the scope of the invention.

References

Abe et al., *J. Biol. Chem.* 262:16793 (1987)
Ahmadi, M. R., S. Raeisi, A. M. N. Dawaji, (2000) Introduction of rapeseed (*Brassica napus* L.), cultivar Talaye. Seed and Plant. 16 (1): Pe127-Pe129, en14. Seed and Plant Improvement Institute, P.O. Box 4119, Karaj 31585, Iran.

Ahmadi, M. R., G. Arab, S. Raeisi, E. Mohammadi, M. Khiavi, S. Pourdad, M. J. Fagheeh, A. Hekmat-Gharabagh, A. Taee, (2000) Introduction of rapeseed (*Brassica napus* L.), cultivar Esteghlal. Seed and Plant. 16 (1): Pe127-Pe126, en13. Seed and Plant Improvement Institute, P.O. Box 4119, Karaj 31585, Iran.

Baocheng Hu, F Chen, Q Li, X Wu, S Hou, W Fei and X Wang 1999. Effect of cultural control on rapeseed stem rot (*Sclerotinia sclerotiorum*) in *Brassica napus*. Proceedings of the 10th International Rapeseed Congress, Canberra Australia.

BaoMing, Tian, Zhang ShuFen, Song WenGung, Wen YanCheng, Ren LeJian, Wang JianPing, Liu JianMing, (1999) Breeding of "YuYou 4"—a new double—low hybrid of rapeseed (*Brassica napus* L.). Chinese Journal of Oil Crop Sciences. 4:12-14. Institute of Industrial Crops, Henan Academy of Agricultural Sciences, Zhengzhou, Henan 450002, China.

Bardin, S. D. and H. C. Huang. (2001) Research on biology and control of *Sclerotinia* diseases in Canada. Canadian Journal of Plant Pathology 23:88-98.

Barsby, T. L., et al., "A Rapid and Efficient Alternative Procedure for the Regeneration of Plants from Hypocotyl Protoplasts of *Brassica napus*", Plant Cell Reports, (Spring 1996)

Beachy et al., *Ann. Rev. Phytopathol.* 28:451 (1990)

Bernardo, R. and A. L. Kahler, 2001, Theor. Appl. Genet 102:986-992

Binding (1985) Regeneration of Plants, Plant Protoplasts, CRC Press Baco Raton pp 21-73

Boland and Hall (1987) Evaluating soybean cultivars for resistance to *Sclerotinia sclerotiorum* under field conditions. Plant Disease 71:934-936.

Boland and Hall Index of plant hosts of *Sclerotinia sclerotiorum*. Can. J. Plant Pathol. 16:93-108 (1994)

Botella et al., *Plant Molec. Biol.* 24: 757 (1994)

Bradley et al. *Plant Disease* 90(2):215-219 (2006)

Briggs, S., Current Biology, 5(2) (1995)

Brun, H., M. Tribodet, M. Renard, J. Plesis and X. Tanguy, (1987) A field study of rapeseed (*Brassica napus*) resistance to *Sclerotinia sclerotiorum*—7$^{th}$ International Rapeseed Congress, Poznan, Poland Bushnell et al., Can. J. of Plant Path. 20(2):137-149 (1998)

Buzzell, R. I., Welacky, T. W., and Anderson, T. R. (1993) Soybean cultivar reaction and row width effect on *Sclerotinia* stem rot. Can. J. Plnt Sci. 73:1169-1175.

"Cell Culture techniques and Canola improvement" J. Am. Oil Chem. Soc. 66, 4, 455

ChunYun, Guan, FangQiu Li, Xun Li, SheYuan Chen, GuoHuai Wang, ZhongSong Liu, (2003) Resistance of the double-low rapessd cultivar Xiangyou 15 (*B. napus*) to *Sclerotinia sclerotiorum*. Acta Agronomica Sinica. 29 (5): 715-718. Oilseed Corps Institute, Hunan Agricultural University, Changsha, Hunan 410128, China.

Chuong et al., "A Simple Culture Method for *Brassica* hypocotyl Protoplasts", *Plant Cell Reports* 4:4-6 (1985)

Cornelissen and Melchers, Pl. Physiol. 101:709-712, (1993)

Delourme et al., (1991) Radish Cytoplasmic Male Sterility in Rapeseed: Breeding Restorer Lines with good Female Fertility Proc. 8th Int. Rapeseed Conf. Saskatoon Canada 1506-1510.

Elliot et al., *Plant Molec. Biol.* 21:515 (1993)

Evans et al., (1983) Protoplast isolation and Culture, Handbook of Plant Cell Culture MacMillan Publishing Company pp. 124-176.

Fisher et al., *Plant Physiol.* 102:1045 (1993)

Fitt et al. World-wide importance of *phoma* stem canker (*Leptosphaeria maculans* and *L. biglobosa*) on oilseed rape (*Brassica napus*) (2006) European J of Plant Pathology 114:3-15

Fu, S. Z, (1990) New thinking on rape breeding for high yield and disease resistance—breeding a petalless genotype. Acta Agriculture Shanghai. 6 (3):76-77. Economic Crop Research Institute, Jiangsu Province Academy of Agricultural Sciences, Nanjing 210024, China.

Geiser et al., *Gene* 48:109 (1986)

Glick and Thompson, METHODS IN PLANT MOLECULAR BIOLOGY AND BIOTECHNOLOGY 269-284 (CRC Press, Boca Raton, 1993)

Glick, B. R. and Genetic Transformation for the improvement of Canola World Conf, Biotechnol Fats and Oils Ind. 43-46, 1988.

Griess et al., *Plant Physiol.* 104:1467 (1994)

Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119

Hammock et al., Nature 344:458 (1990)

Hansen, N. J. P. & Andersen, S. B. 1996 In vitro chromosome doubling potential of colchicine, oryzalin, trifluralin and APM in *Brassica napus* microspore culture. *Euphytica* 88:159-164

HanZhong, Wang, GuiHua Liu, YuanBen Zheng, XinFa Wang, Qing Yang, (2004) Breeding of the *Brassica napus* cultivar Zhongshuang 9 with high resistance to *Sclerotinia sclerotiorum* and dynamics of its important defense enzyme activity. Scientia Agricultura Sinica. 37(1):23-28. Institute of Oil Corps Research, Chinese Academy of Agricultural Sciences, Wuhan 430062, China.

Hayes et al., *Biochem. J.* 285:173 (1992)

Heney and Orr, *Anal. Biochem.* 114:92-6 (1981)

Heran et al., The effect of Petal Characteristics, Inoculum Density and Enviromental Factors on Infection of Oilseed Rape by *Sclerotinia Sclerotiorum*, The Regional Institute Ltd. (1999)

Hind-Lanoiselet na dLewington, Canola Concepts: Managing *Sclerotinia*. NSW Agriculture Agnote DPI-490 (2004).

Huub et al., *Plant Molec. Biol.* 21:985 (1993)

J. K. Daun et al. *J. Amer. Oil Chem. Soc.,* 60:1751 to 1754 (1983)

Jaynes et al., *Plant Sci.* 89:43 (1993)

G. Johnson, Flowering Fungicides Prove Their Worth Crops ABI/INFORM Trade & Industry, page 14. (2005)

Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase)

Jurke, C. and D. Fernando, (2003) Plant Morphology of Canola and its Effects on *Sclerotinia sclerotiorum* infection in ICPP 2003 8$^{th}$ International Congress of Plant Pathology New Zealand.

Kartha, K. et al., "In vitro Plant Formation from Stem Explants of Rape", *Physiol. Plant,* 31:217-220 (1974)

Kawalleck et al., *Plant Molec. Biol.* 21:673 (1993)

Knultzon et al., *Proc. Nat'l. Acad. Sci. USA* 89:2624 (1992)

Kramer et al., *Insect Biochem. Molec. Biol.* 23:691 (1993)

Lamb et al., *Bio/Technology* 10:1436 (1992).

Lee et al., *EMBO J.* 7:1241 (1988),

Leemans et al. De Greef et al., *Bio/Technology* 7:61 (1989)

Li, Y., G. Kiddle, R. N. Bennett, R. M. Wallsgrove, (1999) Local and systemic changes in glucosinolates in Chinese and European cultivars of oilseed rape (*Brassica napus* L.)

after inoculation with *Sclerotinia sclerotiorum* (stem rot). Annals of Applied Biology. 134 (1):45-58.

Li, Y., J. Chen, R. Bennett, G. Kiddle, R. Wallsgrove, Y. Huang and Y. He (1999) Breeding, inheritance, and biochemical studies on *Brassica napus* cv. Zhongyou 821: tolerance to *Sclerotinia sclerotiorum* (stem rot) 10$^{th}$ International Rapeseed Congress, Canberra, Australia Liu, C., D. Du, Y. Huang, C. Wand, (1991) Study on tolerance to *Sclerotinia* slerotiorum and the hereditary properties in *Brassica-napus*. Scientia Agricultura Sinica. 24(3):43-49.

Liu, LiangHong, ShuWen Shi, JiangSheng Wu, YuXia Chen, YongMing Zhou, (2003) Mutation induction and in vitro screening for stem rot resistant/tolerant materials with oxalic acid in rape (*Brassica napus* L.). Chinese Journal of Oil Crop Sciences. 25(1):5-8, 13. Plant Science and Technology college, Huazhong Agricultural University, Wuhan 430070, Hubei, China.

Logemann et al., *Bio/Technology* 10:305 (1992)

Manitoba Agnueedne, Food and Rural Initiatives (2004)

Marshall et al., *Theor. Appl. Genet.* 83:435 (1992)

Miki et al., "Procedures for Introducing Foreign DNA into Plants" in *Methods in Plant Molecular Biology and Biotechnology*

Miki et al., *Theor. Appl. Genet.* 80:449 (1990)

Mindrinos et al., Cell 78:1089 (1994) (*Arabidopsis* RSP2 gene for resistance to *Pseudomonas syringae*)

Mollers, C., Iqbal, M. C. M. & Robblen, G. 1994 Efficient production of doubled haploid *Brassica napus* plants by colchicine treatment of microspores. *Euphytica* 75:95-104.

Morall et al., Recent progress in chemical control of *Sclerotinia* Stem rot of rape in western Canada. Meded. Fac. Landbouwwet. Rijksuniv. Gent. 50:1189-1194 (1985)

Morisette et al., Abstract #1566, Am. Soc. Pl. Physiol. Meeting 1997

Mullins, E., C. Quinlan, P. Jones, (1999) Isolation of mutants exhibiting altered resistance to *Sclerotinia sclerotiorum* from small M2 populations of an oilseed rape (*Brassica napus*) variety. European Journal of Plant Pathology. 105 (5):465-475.

Narasimhulu, S., et al., "Species Specific Shoot Regeneration Response of Cotyledonary Explants of *Brassicas*", *Plant Cell Reports*, (Spring 1988)

Ogura H. et al., (1986) Transfer of Cytoplasmic Male Sterility from Tetraploid Radish *Raphanus sativus* to Raphanobrassica by means of successive backcrosses Memoirs of the Faculty of Agriculture Kagoshima University 22(31):69-72.

Okuyama, Y., S. Hiraiwa, M. Ishida, S. Sugawara, T. Endo, M. Shibata, S. Tanosaki, I. Kaneko, (1995) A new vegetable rape cultivar "Harunokagayaki". Bulletin of the Tohoku National Agricultural Experiment Station. 89:11-20. National Agriculture Research Center, Tsukuba, Ibaraki 305, JAP 3-1-1an.

Pang et al., *Gene* 116:165 (1992)

Parijs et al., *Planta* 183:258-264, (1991)

Pellan-Delourme, R., et al., (1988) *Genome* 30(2):234-238

Pen et al., *Bio/Technology* 10:292 (1992)

Pelletier et al., (1983) *Mol. Gen. Genet.* 191(2):244-250.

Pelletier et al., (1987) Molecular, Phenotypic and Genetic Characterization of Mitochondrial Recombinants in Rapeseed Proc. 7th Int. Rapeseed Conf. Poznau, Poland 113-118

Pratt et al., *Biochem. Biophys. Res. Comm.* 163:1243 (1989)

Przibilla et al., *Plant Cell* 3:169 (1991)

Raboy et al., *Maydica* 35:383 (1990)

Regan, *J. Biol. Chem.* 269:9 (1994)

Rugang, Li, Roger Rimmer, Lone Buchwaldt, G. Andrew Sharpe, Ginette Seguin-Swartz, Cathy Coutu, Dwayne D. Hegedus, (2004) Interaction of *Sclerotinia sclerotiorum* with a resistant *Brassica napu* cultivar: expressed sequence tag analysis identifies genes associated with fungal pathogenesis. *Fungal Genetics and Biology.* 41 (8):735-753.

Sairdan et al., Incidence of white mold and yield of upright bean grown in different planting patterns. *J. Phytopathol.* 137:118-124 (1993)

Sedun, F. S., G. Seguin Swartz, G. F. W. Rakow, (1989) Genetic variation in reaction to *Sclerotinia* stem rot in *Brassica* species. Canadian Journal of Plant Science. 69(1):229-232.

Shiroza et al., *J. Bacteriol.* 170:810 (1988)

Søgaard et al., *J. Biol. Chem.* 268:22480 (1993)

Simmonds et al. Canadian Patent #CA 2145833 Sep. 20, 2005 Induction of Embryogenesis and regeneration of doubled haploids using microtubule inhibitors.

Simmonds et al. U.S. Pat. No. 6,200,808 B1 Mar. 13, 2001 Induction of Embryogenesis from plant microspores Specht, Manuela. High Yields of Winter Oilseed Rape in Germany 2004. Union for the Promotion of Oil and Protein Plants.

Steinmetz et al., *Mol. Gen. Genet.* 200:220 (1985) (nucleotide sequence of *Bacillus subtilis* levansucrase gene)

Sumitani et al., *Biosci. Biotech. Biochem.* 57:1243 (1993).

Sun, ChaoCai, GuangHua Fang, Hua Zhao, WeiRong Wang, YanLi Li, XiaoFang Qian, YinHua Chen, (1998) Study on rapessed quality breeding of *Brassica napus* L. in Shanghai suburbs. Acta Agriculturae Shanghai. 14(3):24-28. Crop Breeding and Cultivation Research Institute, Shanghai Academy of Agricultural Science, Shanghai 201106, China.

Swanson, E., "Microspore Culture in *Brassica*", *Methods in Molecular Biology*, Vol. 6, Chapter 17, p. 159 (1990)

Swanson, E. B., Coumans, M. P., Wu, S. C., Barsby, T. L., Beversdorf, W. D. (1987) Efficient isolation of microspores and the production of microspore-derived embryos from *Brassica napus*. Plant-Cell-Reports. 6(2):94-97.

Tavladoraki et al., *Nature* 366:469 (1993)

Taylor et al., 1994 Abstract #497, Seventh International Symposium on Molecular Plant-microbe Interactions (Edinburgh, Scotland).

Toubart et al., *Plant J.* 2:367 (1992)

Tu (1983) Efficacy of iprodione against *Alternaria* black pod and white mold of white beans. Can. Plant. Path. 5:133-135.

Van Damme et al., *Plant Molec. Biol.* 24:25 (1994)

Van Hartingsveldt et al., *Gene* 127:87 (1993)

Wang J. and R. Bernardo, 2000, Crop Sci. 40:659-665

Weissbach A and H. Weissbach eds. (1988) Methods of Plant Molecular Biology Academic Press Inc.

WeiXin, Fei, Li QiangSheng, Wu XinJie, Hou ShuMin, Chen FengXiang, Wang WenXiang, Hu BaoCheng, (2002) A study on control of *Sclerotinia* blight (*Sclerotinia sclerotiorum*) of rape with agronomic measures. Chinese Journal of Oil Crop Sciences. 24(3):47-49. Crop Research Institute, Anhui Academy of Agricultural Sciences, Hefei 230031, Anhui, China.

Yanyou, Wu, Mu Zhonglin, Luo Peng, (1996) Application of sodium iodacetate in the mutagenesis breeding of *Brassica napus*. Sichuan Daxue Xuebao (Ziran Kexueban). 33(2): 201-205.

YongJu, Huang, Chen Jun, Li YunChang, (2000) Genetic study of *Sclerotinia sclerotiorum* resistance in rapeseed (*Brassica napus* L.) I. Its inheritance and combining ability. Chinese Journal of Oil Crop Sciences. 22(4):1-5. Oil Crops Research Institute, CAAS, Wuhan 430062, Hubei, China.

Yunchang Li, Jun Chen, Richard Bennet, Guy Kiddle, Roger Wallsgrove, Yongju Huang, Yuanhui He 1999 Breeding, inheritance, and biochemical studies on *Brassica napus* cv. Zhongyou 821: Tolerance to *Sclerotinia sclerotiorum* (stem rot). Proceedings of the 10th International Rapeseed Congress, Can berra Australia Zhao, J., A. J. Peltier, J. Meng, T. C. Osborn, C. R. Grau, (2004) Evaluation of *Sclerotinia* stem rot resistance in oilseed *Brassica napus* using a petiole inoculation technique under greenhouse conditions. *Plant Disease.* 88(9): 1033-1039.

Zhao, Jianwei, Jinling Meng, (2003) Genetic analysis of loci associated with partial resistance to *Sclerotinia sclerotiorum* in rapeseed (*Brassica napus* L.). *Theoretical and Applied Genetics.* 106(4):759-764.

Zhou et al., *Pl. Physiol.* 117(1):33-41 (1998)

That which is claimed:

1. *Brassica* line 04SN41415, representative seed of said line having been deposited as NCIMB Accession Number 41388.
2. A seed of the *Brassica* line of claim 1.
3. A plant of the *Brassica* line of claim 1.
4. A plant cell from the plant of claim 3.
5. F1 progeny of the plant of claim 3, wherein said progeny are representative of a population having an SSDI% score which is less than about 60% of the SSDI% score of Pioneer Hi-Bred variety 46A76 or of Pioneer Hi-Bred variety 46A65 or of the mean score of said two varieties, and further wherein said progeny produces seed having a glucosinolate level of less than 30 u moles per gram of oil-free solid and less than 2% erucic acid in the endogenous oil component; wherein a sample of seed of said progeny is deposited as NCIMB accession number 41390.
6. The progeny of claim 5 wherein said progeny is produced by culture of haploid tissue.
7. A method of generating progeny plants, comprising:
   (a) crossing the plant of claim 3 with itself or with another *Brassica* plant to yield seed;
   (b) growing the *Brassica* seed of step (a) to yield a [derived] plant or group of plants; and
   (c) optionally repeating the crossing and growing of steps (a) and (b) for successive generations to produce progeny plants.
8. The method of claim 7, further comprising the step of
   (d) selecting a descendent plant representative of a population having an SSDI% score which is less than about 60% of the SSDI% score of Pioneer Hi-Bred variety 46A76 or of Pioneer Hi-Bred variety 46A65 or of the mean score of said two varieties.
9. A method of producing an oil, comprising:
   (a) crushing seeds produced by the plant of claim 3; and
   (b) extracting a crude oil from such crushed seeds.
10. The method of claim 7, wherein the progeny plant or group plants further representing a population having an average level of blackleg resistance which is greater than that of Pioneer Hi-Bred variety 46A76 under the same environmental and disease conditions.
11. The plant of claim 3 further comprising a transgene.
12. The plant of claim 3 wherein said plant is male sterile.

* * * * *

UNITED STATES PATENT AND TRADEMARK OFFICE
CERTIFICATE OF CORRECTION

PATENT NO. : 7,977,539 B2
APPLICATION NO. : 12/174134
DATED : July 12, 2011
INVENTOR(S) : Igor Falak et al.

Page 1 of 1

It is certified that error appears in the above-identified patent and that said Letters Patent is hereby corrected as shown below:

Column 66, Claim 7, Line 10, "[de-" should be removed;

Column 66, Claim 7, Line 11, "rived]" should be removed; and

Column 66, Claim 10, Line 25, "group plants further representing" should be --group of plants further represents--.

Signed and Sealed this
Twelfth Day of June, 2012

David J. Kappos
*Director of the United States Patent and Trademark Office*